United States Patent

DiNinno

[11] Patent Number: 5,372,993
[45] Date of Patent: Dec. 13, 1994

[54] BRIDGED CARBAPENEM COMPOUNDS, COMPOSITIONS CONTAINING SUCH COMPOUNDS AND METHODS OF USE

[75] Inventor: Frank P. DiNinno, Old Bridge, N.J.

[73] Assignee: Merck & Co., Inc., Rahway, N.J.

[21] Appl. No.: 74,905

[22] Filed: Jun. 10, 1993

[51] Int. Cl.$^5$ .................. A01N 43/00; A61K 31/395; C07D 487/00
[52] U.S. Cl. ...................... 514/210; 540/302
[58] Field of Search ................ 540/302; 514/210

[56] References Cited

FOREIGN PATENT DOCUMENTS

0416953A2 3/1991 European Pat. Off. .
0422596A3 4/1991 European Pat. Off. .
0517065A1 12/1992 European Pat. Off. .

Primary Examiner—Johann Richter
Assistant Examiner—Rebecca Cook
Attorney, Agent, or Firm—Richard C. Billups; Mark R. Daniel; Joseph F. DiPrima

[57] ABSTRACT

Carbapenems of the formula

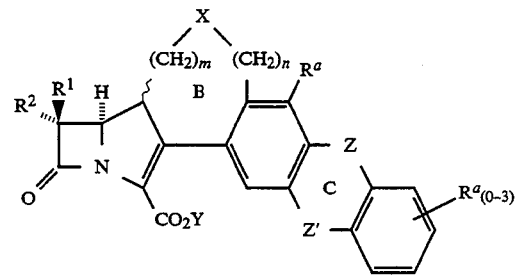

are useful antibacterial agents. Compositions containing such compounds and methods of use are also disclosed.

17 Claims, No Drawings

BRIDGED CARBAPENEM COMPOUNDS, COMPOSITIONS CONTAINING SUCH COMPOUNDS AND METHODS OF USE

BACKGROUND OF THE INVENTION

The present invention relates to antibacterial agents of the carbapenem class in which the five membered ring of the carbapenem nucleus is fused to a multi-ring group which is substituted with various neutral substituents. The fused ring compounds are described in detail below.

Thienamycin was an early carbapenem antibacterial agent having a broad spectrum: it has the following formula:

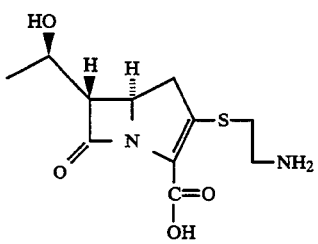

Later, N-formimidoyl thienamycin was discovered; it has the formula:

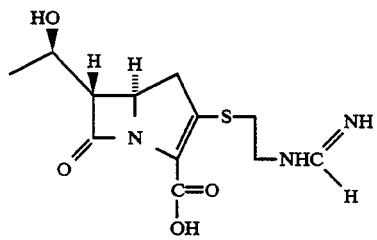

U.S. Pat. Nos. 5,011,832 and 5,025,006 relate to carbapenems of the structure shown below which exhibit antimicrobial activity against strains of methicillin resistant staphylococci (MRSA). The carbapenems described therein possess a meta-disposed biphenyl moiety attached to the C-2 position of the carbapenem ring.

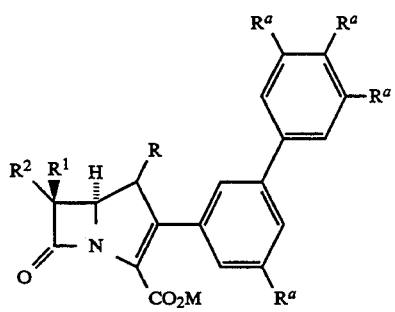

U.S. Pat. Nos. 4,374,849 and 4,374,879 issued on Feb. 22, 1983 to Christensen, et al. relate to compounds of the formula:

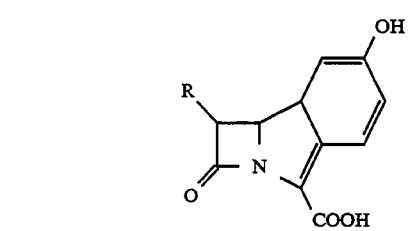

In U.S. Pat. No. 4,374,878, the R group noted above represents a hydroxy substituted ethyl group.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543.257 and 4,260,627 and have the formula:

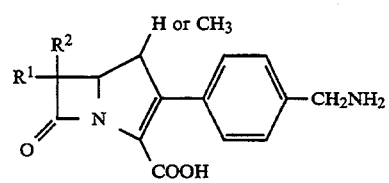

Compounds of the formula:

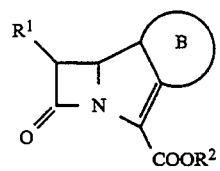

have been disclosed in EPO 422,596 A3 published on Apr. 17, 1991.

European Publication No. 416 953 A3 published on Mar. 13, 1991 addresses compounds of the formula:

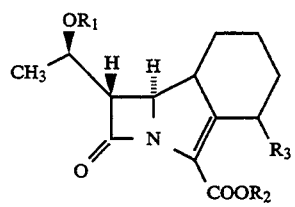

European Publication No. 517 065 A1 published on Dec. 9, 1992 addresses compounds of the formula:

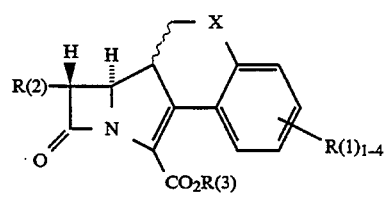

The carbapenems of the present invention are effective against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens.

Moreover, there is an increasing need for agents effective against such pathogens (MRSA/MRCNS) which are at the same time safe, i.e., relatively free from undesirable side effects. And, the current agent of choice, vancomycin, a glycopeptide antibacterial, is experiencing an ever increasing amount of resistance in the MRSA/MRCNS pathogens.

SUMMARY OF THE INVENTION

The present invention addresses a compound represented by formula I:

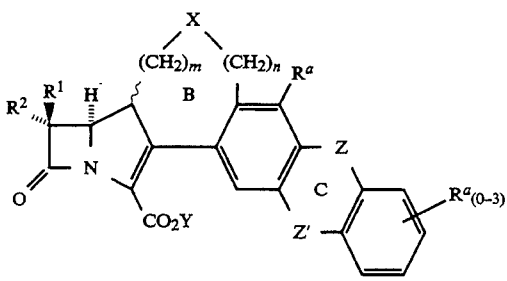

wherein:

m is an integer 0, 1, 2, 3, 4 or 5;

n is an integer 0, 1, 2, 3 or 4;

X represents (a) a bond; (b) —O—; (c) —S(O)$_x$— with x equal to 0, 1 or 2; (d) —C(O)—; (e) —NR'— with R' representing H, C$_1$ to C$_4$ alkyl, acetyl or C$_{1-4}$ alkyl substituted with R$^q$; (f) —CH=CH—; (g) —C(O)NR'—; (h) —NR'C(O)—; (i) —CO$_2$— (j) —OC(O)—; (k) —SO$_2$NR'— or (l) —NR'SO$_2$—.

The values of m, n and X are selected such that ring B constitutes a 6 to 10 membered ring.

Y represents H, a negative charge, a pharmaceutically acceptable ester, a biolabile ester, a carboxylate protecting group or a metal cation.

R$^1$ and R$^2$ independently represent H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$— or (CH$_3$)$_2$CF—.

One of Z and Z' represents a bond and the other represents one of: —CH=CH—, —C(O)NR$^f$—, —NR$^f$C(O)—, —S(O)$_x$NR$^f$—, —NR$^f$S(O)$_x$—, —C(O)—, —OC(O)—, —C(O)O—, —O—, —S(O)$_x$—, with x=0, 1 or 2, or —NR$^f$—, with R$^f$ representing H, C$_{1-4}$ alkyl, —C(O)—C$_{1-4}$ alkyl, —C(O)C$_{1-4}$ alkyl substituted with R$^q$, such that ring C is a 5 or 6 membered ring. R$^q$ represents —OH, —OCH$_3$, —CN, —F, —CF$_3$ or —CO$_2$M$^a$ with M$^a$ representing H, alkali metal or methyl.

Each R$^a$ independently represents hydrogen or a member selected from the group consisting of:

a) trifluoromethyl group which is —CF$_3$;

b) a halogen atom selected from the group consisting of —Br, —Cl, —F and —I;

c) C$_1$-C$_4$ alkoxy radical which is —OC$_{1-4}$ alkyl, wherein the alkyl is optionally mono-substituted by R$^q$, where R$^q$ is as defined above;

d) a hydroxy group which is —OH;

e) a carbonyloxy radical which is —OC(O)R$^s$, where R$^s$ is C$_{1-4}$ alkyl or phenyl, each of which is optionally mono-substituted by R$^q$ as defined above;

f) a carbamoyloxy radical which is —OC(O)N(R$^y$)R$^z$, where R$^y$ and R$^z$ are independently H, C$_{1-4}$ alkyl, (optionally mono-substituted by R$^q$ as defined above), or are taken together to represent a 3- to 5-membered alkylidene radical which forms a ring (optionally substituted with R$^q$ as defined above), or a 2- to 4-membered alkylidene radical interrupted by —O—, —S—, —S(O)— or —S(O)$_2$— which forms a ring, said ring being optionally mono-substituted with R$^q$ as defined above:

g) a sulfur radical which is —S(O)$_n$—R$^s$, where n=0–2, and R$^s$ is defined above;

h) a sulfamoyl group which is —SO$_2$N(R$^y$)R$^z$, where R$^y$ and R$^z$ are as defined above;

i) azido: N$_3$ j) a formamido group which is —N(R$^t$)C(O)H, where R$^t$ is H or C$_{1-4}$ alkyl, said alkyl group being optionally mono-substituted with R$^q$ as defined above;

k) an alkylcarbonylamino radical which is —N(R$^t$)C(O)C$_{1-4}$ alkyl, wherein R$^t$ is as defined above:

l) an alkoxycarbonylamino radical which is —N(R$^t$)C(O)OC$_{1-4}$ alkyl, where R$^t$ is as defined above;

m) a ureido group which is —N(R$^t$)C(O)N(R$^y$)R$^z$ where R$^t$, R$^y$ and R$^z$ are defined above;

n) a sulfonamido group which is —N(R$^t$)SO$_2$R$^s$, where R$^s$ and R$^t$ are as defined above:

o) a cyano group which is —CN;

p) a formyl or acetalized formyl radical which is —C(O)H or —CH(OCH$_3$)$_2$;

q) an alkylcarbonyl radical wherein the carbonyl is acetalized which is —C(OCH$_3$)$_2$C$_1$-C$_4$ alkyl, where the alkyl is optionally mono-substituted by R$^q$ as defined above;

r) a carbonyl radical which is —C(O)R$^s$, where R$^s$ is as defined above:

s) a hydroximinomethyl radical in which the oxygen or carbon atom is optionally substituted by a C$_1$-C$_4$ alkyl group which is —(C=NOR$^z$)R$^y$ where R$^y$ and R$^z$ are as defined above, except they may not be joined together to form a ring;

t) an alkoxycarbonyl radical which is —C(O)OC$_{1-4}$ alkyl, where the alkyl is optionally mono-substituted by R$^q$ as defined above;

u) a carbamoyl radical which is —C(O)N(R$^y$)R$^z$, where R$^y$ and R$^z$ are as defined above:

v) an N-hydroxycarbamoyl or N(C$_1$-C$_4$ alkoxy)carbamoyl radical in which the nitrogen atom may be additionally substituted by a C$_1$-C$_4$ alkyl group which is —C(O)N(OR$^y$)R$^z$, where R$^y$ and R$^z$ are as defined above, except they may not be joined together to form a ring;

w) a thiocarbamoyl group which is —C(S)N(R$^y$)R$^z$ where R$^y$ and R$^z$ are as defined above:

x) carboxyl which is —COOM$^a$ where M$^a$ is as defined above;

y) thiocyanate which is —SCN;

z) trifluoromethylthio which is —SCF$_3$;

aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;

ab) an anionic function selected from the group consisting of: phosphono [P=O(OM$^a$)$_2$]; alkylphosphono {P=O(OM$^a$)[O(C$_1$–C$_4$ alkyl)]}; alkylphosphinyl [P=O(OM$^a$)—(C$_1$–C$_4$alkyl)]; phosphoramido [P=O(OM$^a$)N(R$^y$)R$^z$ and P=O(OM$^a$)NHR$^x$]; sulfino (SO$_2$M$^a$); sulfo (SO$_3$M$^a$); acylsulfonamides selected from the structures SO$_2$NM$^a$CON(R$^y$)R$^z$; and SO$_2$NM$^a$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, said R$^q$, M$^a$, R$^y$ and R$^z$ being as defined above;

ac) a C$_5$–C$_7$ cycloalkyl group in which one of the carbon atoms in the ring is replaced by a heteroatom selected from O, S, NH, or N(C$_1$–C$_4$ alkyl) and in which one additional carbon may be replaced by the NH or N(C$_1$–C$_4$ alkyl), and in which at least one carbon atom adjacent to each nitrogen heteroatom has both of its attached hydrogen atoms replaced by one oxygen thus foraging a carbonyl moiety and there are one or two carbonyl moieties present in the ring;

ad) a C$_2$–C$_4$ alkenyl radical, optionally mono-substituted by one of the substituents a) to ac) above and phenyl which is optionally substituted by R$^q$ as defined above;

ae) a C$_2$–C$_4$ alkynyl radical, optionally mono-substituted by one of the substituents a) to ac) above:

af) a C$_1$–C$_4$ alkyl radical;

ag) a C$_1$–C$_4$ alkyl group mono-substituted by one of the substituents a)–ac) above;

ah) a 2-oxazolidinonyl moiety in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono-substituted by one of the substituents a) to ag) above.

Novel compositions, intermediates, processes of manufacture and methods of treatment are also disclosed.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, W, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused The term "alkenyl" refers to a hydrocarbon radical straight, branched or cyclic containing from 2 to 10 carbon atoms and at least one carbon to carbon double bond. Preferred alkenyl groups include etenyl, propenyl, butenyl and cyclohexenyl.

The term "alkynyl" refers to a hydrocarbon radical straight, branched or cyclic, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, groups as well as rings which are fused, e.g., naphthyl, phenanthrenyl and the like. Aryl thus contain at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted with R$^a$ and W groups as defined below. Preferred substituted aryls include phenyl and naphthyl substituted with one or two preferred R$^a$ or W groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms, said heteroaryl group being optionally substituted with up to four R$^q$ groups.

Heteroaryl thus includes aromatic and partially aromatic groups which contain one or more heteroatoms. Examples of this type are pyrrole, pyridine, oxazole, thiazole and oxazine. Additional nitrogen atoms may be present together with the first nitrogen and oxygen or sulfur, giving, e.g., thiadiazole. The preferred heteroaryls are those where only nitrogen heteroatoms are present when there is more than one. Typical of these are pyrazole, tetrazole, imidazole, pyridine, pyrimidine and pyrazine and triazine.

The heteroaryl group of R$^x$ may be optionally substituted by R$^q$, as defined above, and substitution can be on one of the carbon atoms or one of the heteroatoms, although in the latter case certain substitutent choices may not be appropriate.

The term "heterocycloalkyl" refers to a cycloalkyl group (nonaromatic) in which one of the carbon atoms in the ring is replaced by a heteroatom selected from O, S, NH, or N(C$_1$–C$_4$ alkyl), and in which up to three additional carbon atoms may be replaced by said hetero groups.

The term "tertiary nitrogen" refers to a trivalent uncharged nitrogen atom.

The term "heteroatom" means N, S, or O, selected on an independent basis.

Alkylene (alkylidene or alkanediyl) and arylene refer to the groups noted above with divalent points of attachment. For example. phenylene is an arylene group, attached at any of the 1, 2- 1, 3- or 1, 4-positions. Examples of alkylene include —CH$_2$—, —CH$_2$CH$_2$—, —CH$_2$CH$_2$CH$_2$—,

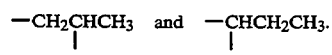

Alkanediyl groups contain from five to fifteen carbon atoms, which may be straight, branched, cyclic or multicyclic.

Aralkyl is a specie of substituted alkyl, containing up to three aryl groups substituted on a straight, branched or cycloalkyl group. The most preferred aralkyl group is benzyl.

Halogen, or "halo" refers to bromine, chlorine, fluorine and iodine.

Alkoxy refers to $C_1$–$C_4$ alkyl—O—, with the alkyl group optionally substituted with the variable $R^q$.

Carbonyloxy refers to the radical: —OC(O)$R^s$, where $R^s$ is $C_{1-4}$ alkyl or phenyl, each of which is optionally mono substituted by $R^q$.

Carbamoyloxy refers to the radical: —OC(O)N($R^y$)$R^z$, where $R^y$ and $R^z$ are independently H, $C_{1-4}$ alkyl, (optionally mono-substituted by $R^q$ as defined above). Alternatively, $R^y$ and $R^z$ can be taken together to represent a 3- to 5-membered alkylidene radical which forms a ring (optionally substituted with $R^q$ as defined above), or a 2- to 4-membered alkylidene radical interrupted by —O—, —S—, —S(O)— or —S(O)$_2$— which forms a ring, said ring being optionally mono-substituted with $R^q$ as defined above.

The term "sulfur radical" refers to the group: —S(O)$_x$—$R^s$, where x is an integer of from 0 to 2, and $R^s$ is as defined above.

The term "sulfamoyl group" refers to: —SO$_2$N($R^y$)$R^z$, where $R^y$ and $R^z$ are as defined above, representing H, alkyl or alkyl monosubstituted with $R^q$.

The term "azido" refers to the group: N$_3$.

The term "formamido" refers to the group:—N($R^t$)-C(O)H, where $R^t$ is H or $C_{1-4}$ alkyl, said alkyl group being optionally mono-substituted with $R^q$ as defined above.

The term "alkylcarbonylamino" refers to the group: —N($R^t$)C(O)$C_{1-4}$ alkyl, wherein $R^t$ is as defined above.

The term "alkoxycarbonylamino" refers to the group: —N($R^t$)C(O)O$C_{1-4}$ alkyl, where $R^t$ is as defined above. The term "ureido" refers to the group: —N($R^t$)-C(O)N($R^y$)$R^z$ where $R^t$, $R^y$ and $R^z$ are defined above.

The term "sulfonamido" refers to the group: —N($R^t$)SO$_2R^s$, where $R^s$ and $R^t$ are as defined above.

The terms "formyl" and "acetalized formyl radical" refer to the groups: —C(O)H or—CH(OCH$_3$)$_2$, respectively. Thus, an alkylcarbonyl radical wherein the carbonyl is acetalized is of the formula: —C(OCH$_3$)$_2$$C_1$–$C_4$ alkyl, where the alkyl is optionally mono-substituted by $R^q$.

A "carbonyl radical" is represented by the formula: —C(O)$R^s$, where $R^s$ is as defined above.

A "hydroximinomethyl" radical in which the oxygen or carbon atom is optionally substituted by a $C_1$–$C_4$ alkyl group is represented by the formula: —(C=NO$R^z$)$R^y$ where $R^y$ and $R^z$ are as defined above, except they may not be joined together to form a ring.

An "alkoxycarbonyl" radical is represented by the formula: —C(O)O$C_{1-4}$ alkyl, where the alkyl is optionally mono-substituted by $R^q$ as defined above.

A "carbamoyl" radical is represented by the formula: —C(O)N($R^y$)$R^z$, where $R^y$ and $R^z$ are as defined.

An N-hydroxycarbamoyl or N($C_1$–$C_4$ alkoxy)carbamoyl radical in which the nitrogen atom may be additionally substituted by a $C_1$–$C_4$ alkyl group is represented by the formula: —C(O)N(O$R^y$)$R^z$, where $R^y$ and $R^z$ are as defined above, except they may not be joined together to form a ring.

A "thiocarbamoyl group" is represented by the structural formula: —C(S)N($R^y$)$R^z$ where $R^y$ and $R^z$ are as defined above.

A "carboxyl group" is represented by the structural formula: —COO$M^a$ where $M^a$ is as defined above.

The term "tetrazolyl" is a heteroaryl group where the point of attachment is the carbon atom of the tetrazole ring and one of the nitrogen atoms is optionally mono-substituted by an alkali metal or a $C_1$–$C_4$ alkyl optionally substituted by $R^q$.

The term "anionic function" refers to the members of the group: phosphono [P=O(O$M^a$)$_2$]; alkylphosphono {P=O(O$M^a$)-[O($C_1C_4$alkyl)]}; alkylphosphinyl [P=O(O$M^a$)-($C_1$–$C_4$alkyl)]; phosphoramido [P=O(O$M^a$)N($R^y$)$R^z$ and P=O(O$M^a$)NH$R^x$]; sulfino (SO$_2M^a$); sulfo (SO$_3M^a$); acylsulfonamides selected from: SO$_2$N$M^a$CON($R^y$)$R^z$; and SO$_2$N$M^a$CN, where $R^x$ is phenyl or heteroaryl.

The carbapenems of the present invention contain a ring which has been designated "B". Ring B is fused between the carbapenem 5 membered ring and a phenyl ring. Ring B may be from 6 to 10 membered, optionally containing a heteroatom, such as when X represents NR', O or S(O)$_x$ with x equal to an integer, 0, 1 or 2. When X represents NR', the variable group R' may be hydrogen, acetyl, acetyl substituted with $R^q$, or $C_1$ to $C_4$ alkyl, optionally substituted with $R^q$.

Ring B is also formed by the alkylene groups, (CH$_2$)$_m$ and (CH$_2$)$_n$ which may be present. In certain instances, not all values of m and n are included in combination. When X represents a direct bond, the sum of m and n is between 2 and 6. When X represents any of the groups other than a bond, the sum of m and n is from 0 to 5. Thus, ring B constitutes a 6 to 10 membered ring.

Preferred values of m and n are such that ring B is six membered, with X preferably representing a direct bond or a heteroatom, O, S or NH.

Ring C is a 5 or 6 membered ring fused between the two phenyl rings. One of Z and Z' represents a bond, and the other variable represents a vinylene (—CH=CH—) bridge, a carbonyl group, an ester, reverse ester, a heteroatom, e.g., an ether or thioether; sulfoxide, sulfone, or an amine. Also, one of Z and Z' may represent —C(O)N$R^f$—, —NRC(O)—, —S(O)$_x$N$R^f$— or —N$R^f$S(O)$_x$— wherein x represents 0, 1 or 2. $R^f$ represents H, $C_{1-4}$ alkyl,—C(O)$C_{1-4}$ alkyl, —C(O)$C_{1-4}$ alkyl substituted with $R^q$, —NR'C(O)$C_{1-4}$ alkyl or —NR'C(O)$C_{1-4}$ alkyl substituted with $R^q$.

Variables $R^3$ and $R^4$ independently represent H or lower alkyl.

The bond at position one is shown as a wavy line in many instances. This indicates that the configuration of the carbon atom at position one is alpha or beta, or the compound is a mixture of isomers. The preferred configuration is beta.

In the compounds of the present invention, the $R^a$ substituent may contribute to the anti-MSRA/MRCNS activity of the overall molecule, or to the other properties of the molecule.

Some $R^a$ substituents may be distinguishable from others chemically or with respect to the biological properties which they confer. In related compounds, it has been found that the charged compounds may afford greater water solubility and reduced potential for CNS side effects. Substituents which tend to confer improved water solubility on the overall compound have been found useful, since they are contemplated to improve the pharmacokinetics of the compound involved. Although a substantial number and range of $R^a$ substituents has been described herein, all of these are contemplated to be a part of the present invention in connection with the genus of formula I.

When a group is termed "substituted", unless otherwise indicated, this means that the group contains from 1 to 3 substituents $R^q$ thereon. With respect to alkyl groups, the substituents thereon are selected from the variables specified for $R^a$. Preferred substituent groups include $C_{1-4}$ alkyl, $C_{2-6}$ alkenyl, $C_{2-6}$ alkynyl, hydroxy, $C_{1-4}$ alkoxy, aryl, heteroaryl, aralkyl, halo, cyano, nitro, carboxyl and the anionic function groups, as these terms are defined above.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as McOmie, J. (ed) *Protecting Groups in Organic Chemistry* pp. 46–119 (1973).

The preferred compounds of the invention include compounds wherein $R^1$ represents H. In the most prefered compounds $R^1$ represents H, and $R^2$ represents (R)CH$_3$CH(OH)—. The designation (R) defines the absolute configuration of the stereocenter.

The preferred compounds of the invention also include compounds where the $R^a$ variables represent H, halo, alkylthio, alkylsulfonyl or cyano.

The preferred compounds also include compounds where ring B has 6 or 7 atoms.

One preferred subgenus included in the invention relates to compounds represented by structural formula Ia:

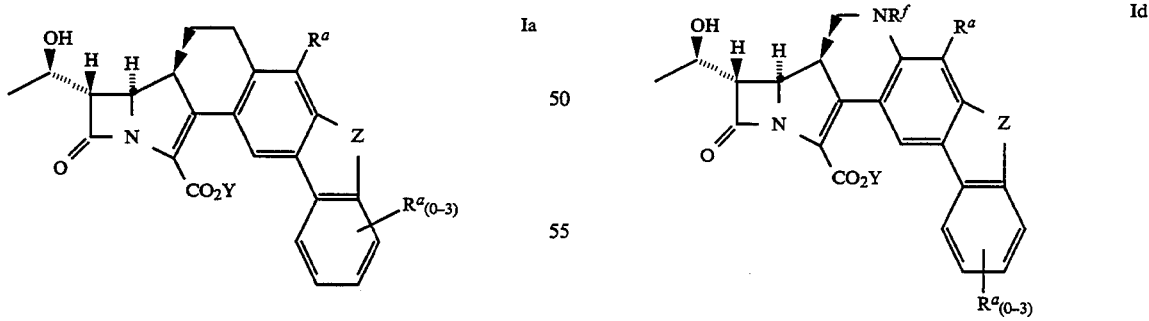

wherein one $R^a$ represents a group a) through ah) and the other $R^a$ groups represent hydrogen; Y represents H, a biolabile ester, a pharmaceutically acceptable cation or a negative charge, and Z represents —C(O)—, —O— or —S(O)$_x$ with x equal to zero.

Another preferred subgenus included in the invention relates to compounds represented by structural formula Ib:

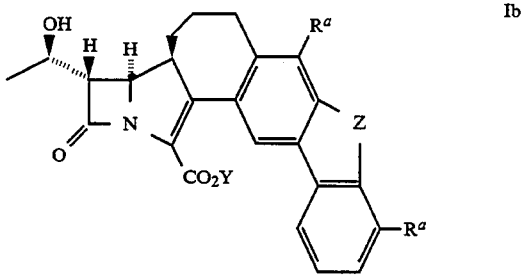

wherein the values of Y, Z and $R^a$ are as described above with respect to formula Ia.

Another preferred subgenus included in the invention relates to compounds represented by structural formula Ic

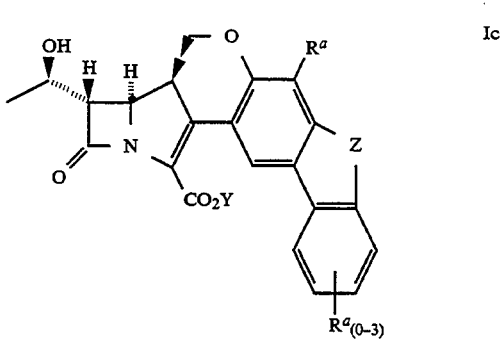

wherein the values of Y, Z and $R^a$ are as described above with respect to formula Ia.

Another subgenus included in the invention relates to compounds represented by structural formula Id:

wherein the values of Z, Y and $R^a$ are as described above with respect to formula Ia, and the $R^f$ substituent group on the nitrogen represents hydrogen, methyl, hydroxy or C1–4 alkoxy.

Another subgenus included in the invention relates to compounds represented by structural formula Ie:

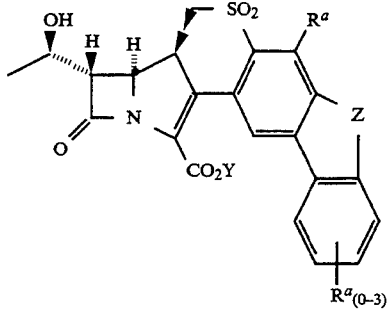

wherein the values of Z, Y and $R^a$ are as described above with respect to formula Ia.

Another subgenus included in the invention relates to compounds represented by structural formula If:

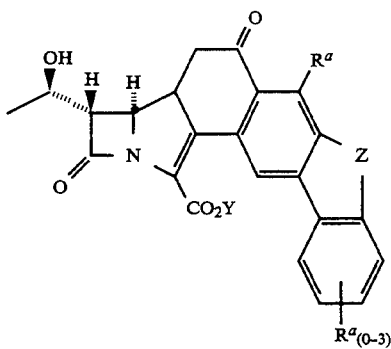

wherein the values of Z, Y and $R^a$ are as described above with respect to formula Ia.

Another subgenus included in the invention relates to compounds represented by structural formula Ig:

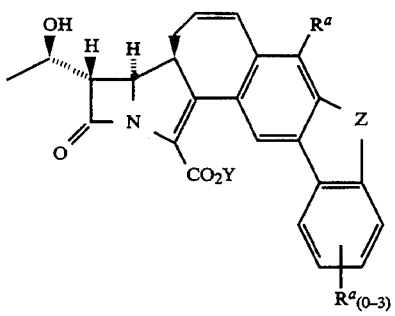

wherein the values of Z, Y and $R^a$ are as described above with respect to formula Ia.

Another subgenus included in the invention relates to compounds represented by structural formula Ih:

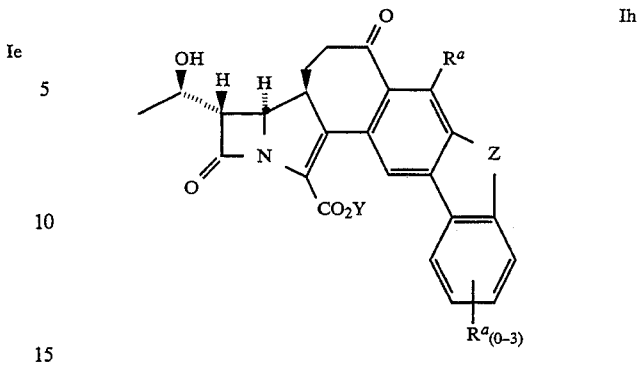

wherein the values of Z, Y and $R^a$ are as described above with respect to formula Ia.

In X, when X represents $S(O)_x$, the preferred values of x are zero and two, and when X represents NR', the preferred value of R' is H.

in $R^a$, when these variables represent alkoxy substituted with $R^q$, the preferred $R^q$ values are —OH, —OCH$_3$, —CF$_3$ and —CO$_2$M$^a$. In —COOM$^a$, the preferred values of $M^a$ are H and methyl.

When $R^a$ represents —OC(O)$R^s$, the preferred $R^s$ values are $C_{1-4}$alkyl and substituted $C_{1-4}$alkyl.

When $R^a$ represents —OC(O)NR$^y$R$^z$, the preferred $R^y$ and $R^z$ values are H, lower alkyl and $C_{4-5}$ alkylidene.

When $R^a$ represents —S(O)$_x$—$R^s$, x preferably is zero, and $R^s$ is preferably alkyl.

When $R^a$ represents —SO$_2$NR$^y$R$^z$, $R^y$ and $R^z$ preferably represent H, lower alkyl or are taken together to represent a $C_{4-5}$ alkylidene group.

When $R^a$ represents —N(R$^t$)C(O)H, —N(R$^t$)C(O)C$_{1-4}$ alkyl or substituted alkyl, —N(R$^t$)C(O)OC$_{1-4}$ alkyl or substituted alkyl, —N(R$^t$)C(O)NR$^y$R$^z$ or —NR$^t$-SO$_2$R$^s$, the preferred $R^t$ groups are H and $C_{1-4}$ lower alkyl.

When $R^a$ represents a $C_{5-7}$ cycloalkyl group where one carbon is replaced with a heteroatom, —NH—, O, or —S(O)$_x$—, the preferred heteroatom is nitrogen, either —NH— or —N(C$_{1-4}$alkyl)—.

When $R^a$ represents an alkenyl group, the preferred alkenyl group is allyl, —CH$_2$CH=CH$_2$.

Among the more preferred $R^a$ groups are $C_{1-4}$ alkyl mono-substituted with hydroxy, such as, hydroxymethyl; formyl: carbamoyl, such as, —CONH$_2$; cyano; halo, such as iodo; $C_1$ to $C_4$ alkylthio, such as methylthio and its dioxides, such as —SO$_2$CH$_3$; and mono substituted $C_2$ to $C_4$ alkylthio, such as hydroxyethylthio, —SCH$_2$CH$_2$OH.

In addition to the above, examples of the more preferred $R^a$ groups include:

| | |
|---|---|
| —OCH$_3$ | —OCH$_2$CO$_2$Me |
| —OCH$_2$CH$_2$OH | —CF$_3$ |
| —OH | —OC(O)CH$_3$ |
| —OC(O)NH$_2$ | —SCH$_2$CH$_2$OH |
| —S(O)CH$_3$ | —S(O)CH$_2$CH$_2$OH |
| —SO$_2$NH$_2$ | —SO$_2$N(CH$_3$)$_2$ |
| —NHCHO | —NHC(O)CH$_3$ |
| —NHCO$_2$CH$_3$ | —NHSO$_2$CH$_3$ |
| —C(O)CH$_3$ | —COCH$_2$OH |
| —CH=NOH | —CH=NOCH$_3$ |
| —CH=NOCH$_2$CO$_2$Me | —CH=NOCMe$_2$CO$_2$Me |
| —SO$_2$CH$_2$CH$_2$OH | —CO$_2$CH$_2$CH$_2$OH |
| —CH=NOCMe$_2$CO$_2$Me | —C(O)NHCH$_3$ |
| —CH$_2$CO$_2$Me | —C(O)NHCH$_2$CN |
| —C(O)N(CH$_3$)$_2$ | —C(O)NHCH$_2$CO$_2$Me |
| —C(O)NHCH$_2$CONH$_2$ | |

13

-continued

| | |
|---|---|
| —C(O)NHOH | —C(O)NHCH₃ |
| -tetrazoly | —CO₂Me |
| —SCF₃ | —PO₃HMe |
| —C(O)NHSO₂Ph | —C(O)NHSO₂NH₂ |
| —SO₃Me | —SO₂NHCN |
| —SO₂NHCONH₂ | —CH=CHCN |
| —CH=CHC(O)NH₂ | —CH=CHCO₂Me |
| —C≡C—C(O)NH₂ | —C≡C—CN |
| —CH₂N₃ | and |
| —CH₂I. | |

Listed below are the more preferred compounds of the invention. The following numbering system applies:

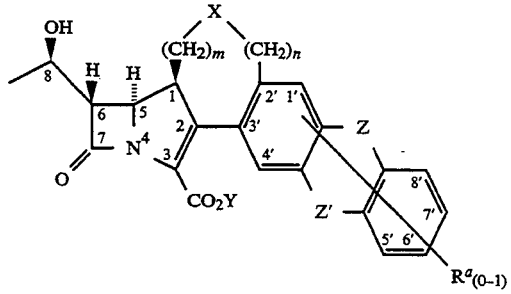

wherein the representation of $R^a$ includes attachment in either aromatic ring, at positions 1', 5', 6', 7' or 8'. The most preferred compounds of the invention include the following:
compounds where m and n represent 1; m represents 1 and n represents zero; and m represents 2 and n represents zero;
X represents a bond, —O—, —S—, —SO₂—, —C(O)—, —NH—, —CH=CH— and —C(O)NH—, wherein the point of attachment to the phenyl ring is through either a carbon or nitrogen atom;
Z and Z' represent —C(O)— and a bond, respectively; —S— and a bond, respectively; —SO₂— and a bond, respectively; —O— and a bond, respectively; —NH— and a bond, respectively; —OC(O) and a bond, respectively, and —(O)CO— and a bond, respectively;
Y represents an alkali metal cation or a biolabile ester.

The compounds of the invention can be synthesized in accordance with the following general schemes and examples.

GENERAL SYNTHESIS OF SUBSTITUTED-PHENYL-SUBSTITUTED TETRALONES

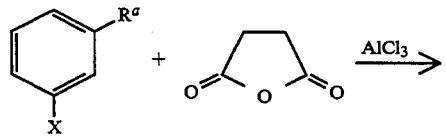

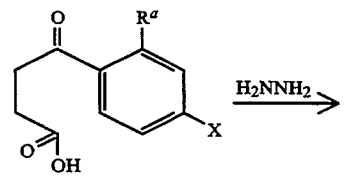

14

-continued
GENERAL SYNTHESIS OF SUBSTITUTED-PHENYL-SUBSTITUTED TETRALONES

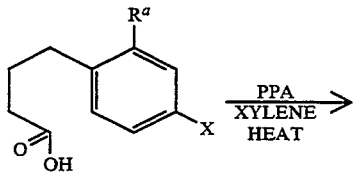

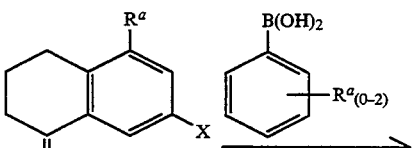

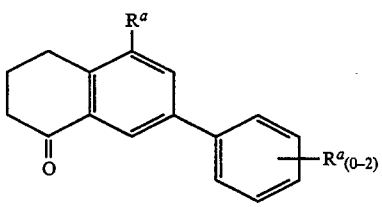

Wherein $R^a$ is as previously defined and X is Br, I, or OTf.
PPA = polyphosphoric acid

GENERAL REGIOSPECIFIC SYNTHESIS OF CYCLOALKANONYL-FLUORENONES

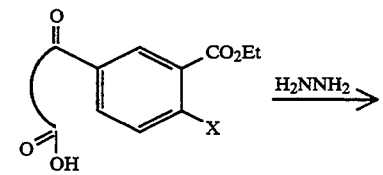

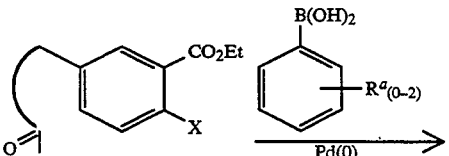

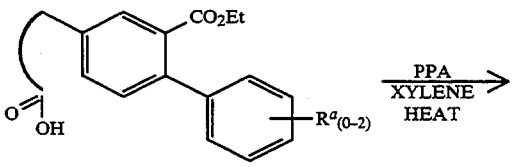

-continued
GENERAL REGIOSPECIFIC SYNTHESIS OF CYCLOALKANONYL-FLUORENONES

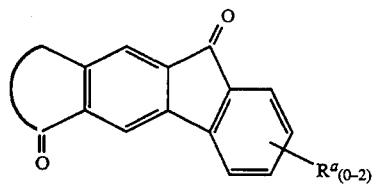

Wherein $R^a$ is as previously defined, n = 2-5, and X is Br, I, or OTf.

GENERAL, REGIOSPECIFIC SYNTHESIS OF CYCLOALKANONOYL-NAPHTHYRIDONES

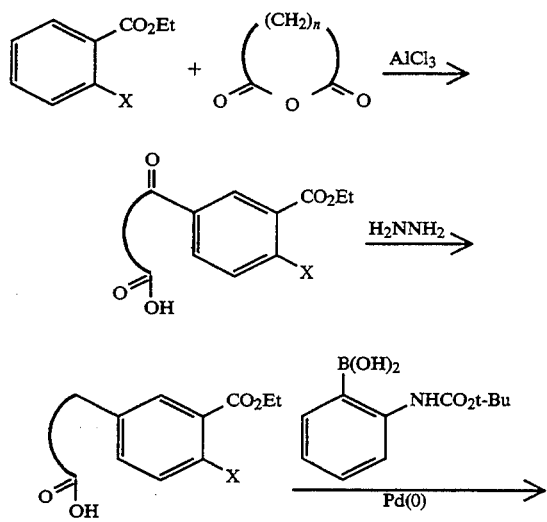

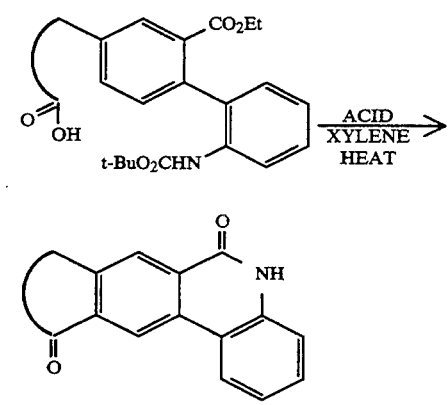

Wherein $R^a$ is as previously defined, n = 2-5, and X is Br, I, or OTf.
    t-Bu = t-butyl    Et = ethyl    OTf = triflate leaving group

GENERAL, REGIOSPECIFIC SYNTHESIS OF CYCLOALKANONOYL-DIBENZOCOUMARINS

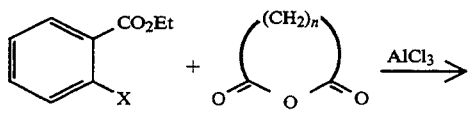

-continued
GENERAL, REGIOSPECIFIC SYNTHESIS OF CYCLOALKANONOYL-DIBENZOCOUMARINS

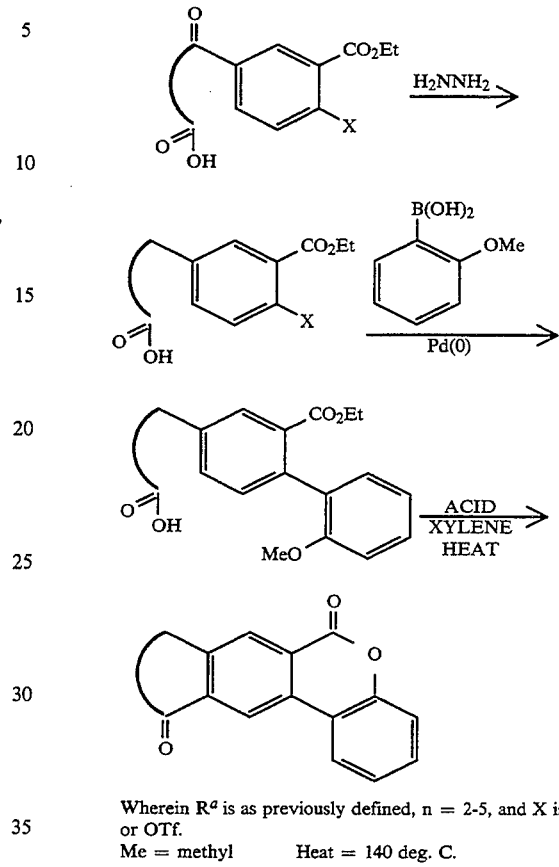

Wherein $R^a$ is as previously defined, n = 2-5, and X is Br, I, or OTf.
Me = methyl    Heat = 140 deg. C.

SYNTHESIS OF SUBSTITUTED-PHENYL-4-OXO-4-H-BENZOPYRAN AND THIOPYRAN

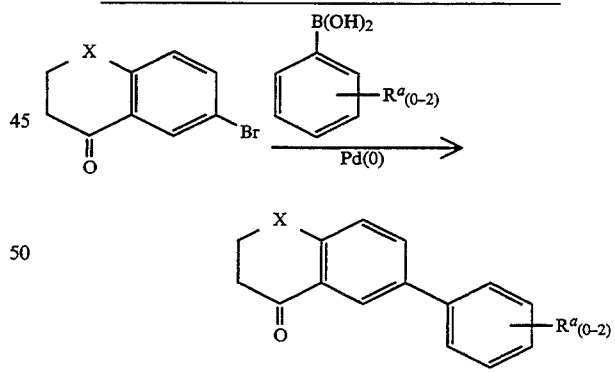

Wherein $R^a$ and X = O, S

SCHEME I
SYNTHESIS OF HEXACYCLIC-HETEROARYL-CARBAPENEMS

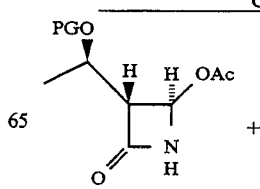

-continued
SCHEME I
SYNTHESIS OF HEXACYCLIC-HETEROARYL-
CARBAPENEMS
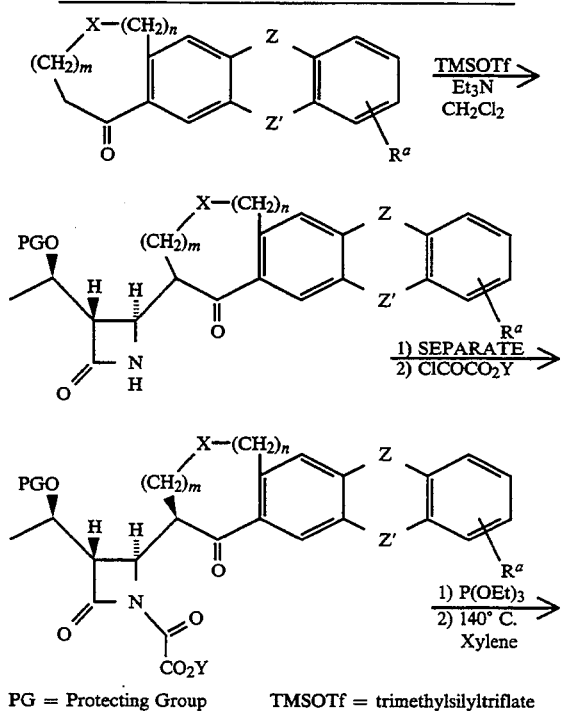
PG = Protecting Group    TMSOTf = trimethylsilyltriflate
-continued
SCHEME I
SYNTHESIS OF HEXACYCLIC-HETEROARYL-
CARBAPENEMS
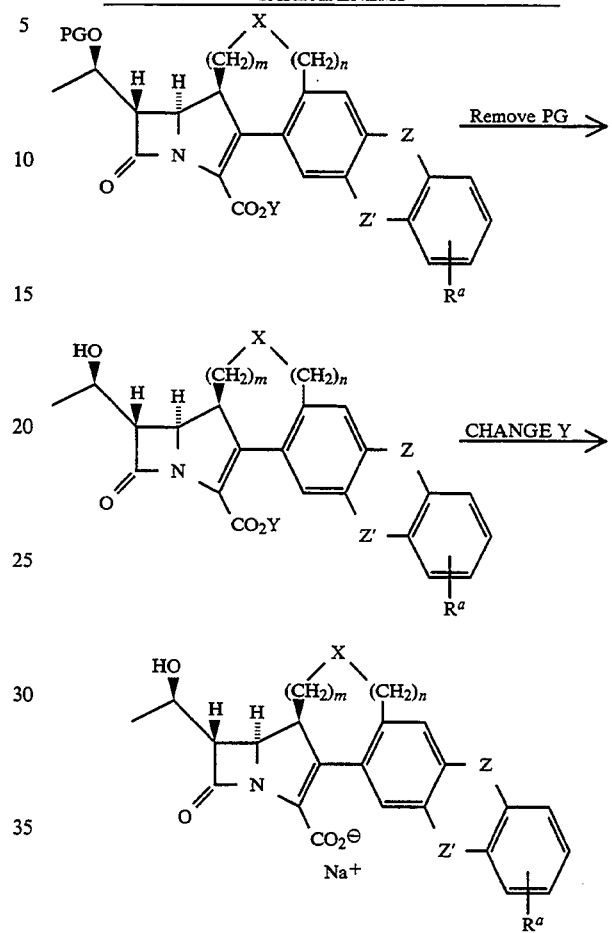
Wherein PG, X, Z, Z', $R^a$, and Y are as previously defined.
SCHEME II
SYNTHESIS OF HEXACYCLIC-
HETEROARYL-CARBAPENEMS
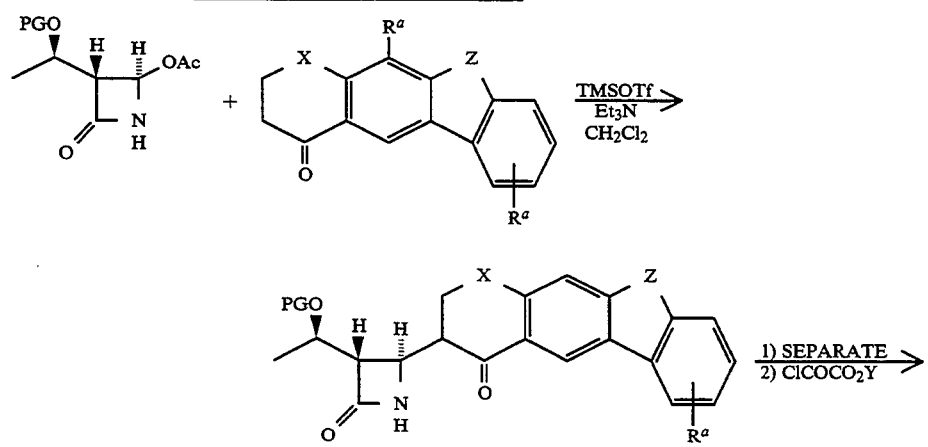

SCHEME II
SYNTHESIS OF HEXACYCLIC-HETEROARYL-CARBAPENEMS
-continued
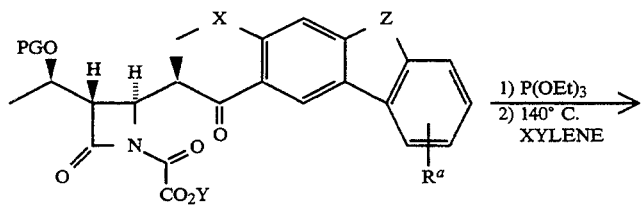
1) P(OEt)$_3$
2) 140° C. XYLENE
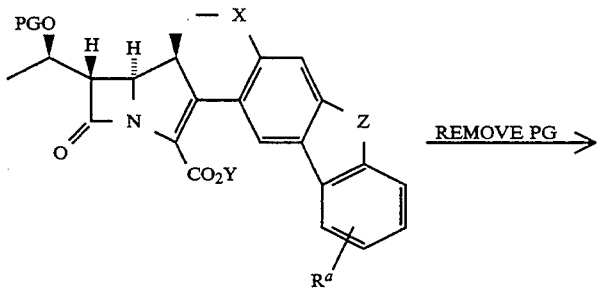
REMOVE PG →
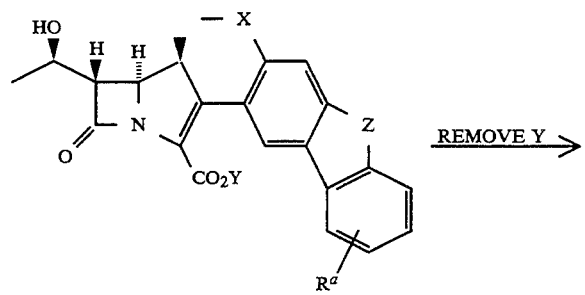
REMOVE Y →
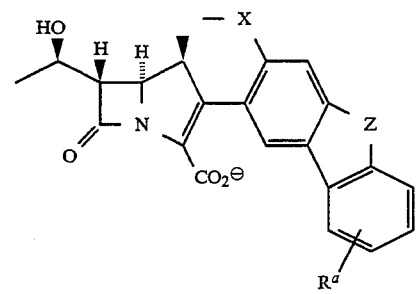
Wherein PG, X, Z, R$^a$, and Y are as previously defined.
SCHEME III. SYNTHESIS OF HEXACYCLIC-HETEROARYL-CARBAPENEMS
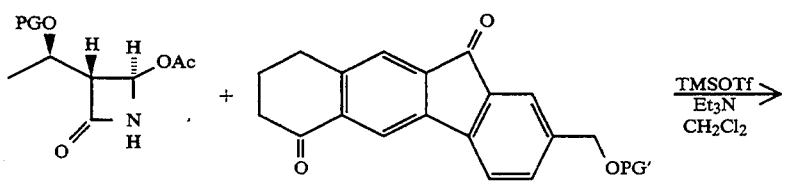
TMSOTf
Et$_3$N
CH$_2$Cl$_2$ →

-continued
SCHEME III. SYNTHESIS OF HEXACYCLIC-HETEROARYL-CARBAPENEMS
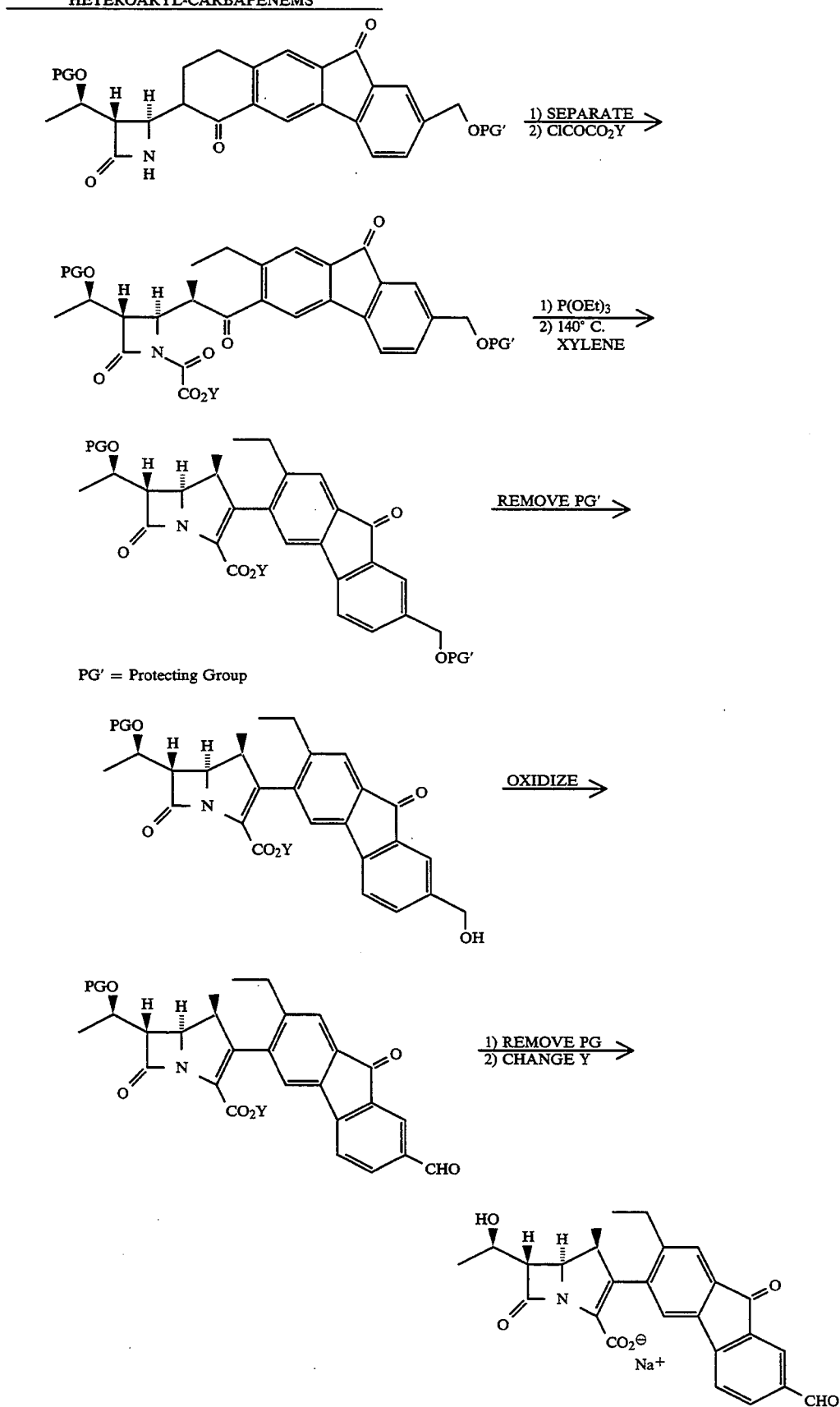
PG' = Protecting Group -continued
SCHEME III. SYNTHESIS OF HEXACYCLIC-
HETEROARYL-CARBAPENEMS Wherein PG, PG' and Y are as previously defined.

The syntheses of compounds I am outlined in Schemes I, II, and III, which depict strategies that progress from the most general to the more specific. Basically, the skeletal arrangement of these molecules can be assembled in three key stages. Initially, the known, appropriately substituted acetoxyazetidinone is reacted with a cycloalkanonylaromatic compound in the presence of a tertiary amine base such as triethylamine, diisopropylethylamine, pyridine or the like, and a silylating agent such as trimethylsilyltrifluoromethanesulfonate, in a solvent such as dichloromethane, acetonitrile or the like, at a temperature of from −23° C. to ambient temperatures, for from 1 to 24 hours, in an inert atmosphere. The reaction is such that the cycloalkanone is converted in situ to its corresponding silylenolether derivative, which in turn reacts with the activated form of the azetidinone, brought about by the the interaction of the acetoxyazetidinone with a relatively small percentage of the trimethylsilyltrifluoromethanesulfonate, to form a carbon-carbon bond from $C_4$ of the azetidinone to the alpha carbon of the cycloalkanone. The latter constitutes a new stereocenter in the adduct, and the ratio of the resulting diastereomers is typically almost equal. The isomers maybe separated by standard techniques and processed individually. Alternatively, the silylenolether derivative of the cycloalkanone may be produced in a separate operation and then brought into interaction with the acetoxyazetidinone derivative and an activating agent or Lewis acid such as trimethylsilyltrifluoromethanesulfonate, zinc chloride, zinc iodide, borontrifluoride etherate, stannous chloride, tin triflate, titanium trichloride, aluminium chloride or the like, in aprotic solvents such as dichloromethane, acetonitrile, benzene, THF, hexane or the like. In this way, the stereochemical outcome of the reaction maybe altered to produce a predominance of one isomer or the other.

The second key stage is the conversion of the newly formed azetidinone to the corresponding Wittig intermediate via the "oxalimide process". This conversion is accomplished in two steps and begins with the reaction of the azetidinone and the known, appropriately protected chlorooxalylester reagent, in the presence of a suitable base such as pyridine, triethylamine or the like, in an inert solvent such a dichloromethane, toluene, or the like, from a temperature of from −23° C. to ambient temperatures, for from a few minutes to several hours. Typically the oxalimide which is rapidly formed is isolated by conventional techniques and may be similarly purified or, more conveniently, used directly in the second step of the process. Here the oxalimide is heated with a large excess (10-20 equivalents) of an alkoxyphosphine reagent such as triethoxyphosphine, diethoxymethylphosphine, or the like, in an inert solvent such as benzene, toluene, xylene or the like, at a temperature of from 50° C. to 120° C. for from a few minutes to several hours. The resulting alkoxyphosphorane intermediate is typically not isolated due to its hydrolytic lability, but instead can be used in situ in the final stage of the synthesis.

The last key stage involves the thermal cyclization of the alkoxyphosphorane intermediate in an inert solvent such as benzene, toluene, xylene or the like, at refluxing temperatures, in an inert atmosphere of nitrogen or helium, in the presence of a trace of hydroquinone, for from an hour to five days.

At this juncture, the remaining number of steps to complete the synthesis of the compounds I of the invention may vary. In cases where a hydroxyl group is present in the group at C-6 of the carbapenem nucleus or on the aromatic C-2 appendage, and it is covered with a protecting group (PG), the protecting group(s) maybe removed by established methods, which are discussed further below. In this instance, and in examples requiring no further chemistry at this stage, the carboxyl protecting group is analogously removed to affect the formation of I. Examples of this procedure are outlined in Schemes I and II. On the other hand, prior to the removal of the carboxyl protecting group, additional chemistry maybe performed which allows for the introduction of functionality consistent with the scope of the invention. For example, Scheme III depicts the selective removal of a benzylic hydroxyl protecting group, followed by oxidation to the corresponding aldehyde group to provide a preferred $R^a$ substituent. This oxidation may be carried out by a variety of methods, such as the Swern or the TPAP (tetra-n-propylammonium perruthenate/N-methylmorpholine N-oxide) oxidation.

Other examples of chemical transformations which can be implemented at the carbapenem stage of the synthesis provide for certain definitions of X and Z, including, e.g., oxidation at a sulfur atom to provide either the corresponding sulfoxide or sulfone.

The starting materials for the initial stage of the foregoing sequence are either known in the an or can be readily prepared by established methods. In this regard the following references may be applicable:

5-phenyl-1-tetralone: K. Itoh, etal, *Chem. Pharm. Bull.*, 32, 130(1984); 6-phenyl-1-tetralone: K. Itoh, etal, ibid.; M. S. Newman and H. V. Zahm, *J. Amer. Chem. Soc.*, 65, 1097(1943); N. L. Allinger and E. S. Jones, *J. Org. Chem.*, 27, 70( 1962); 7-phenyl-1-tetralone: R. Buckle, etal, *J. Medicinal Chem.*, 20, 1059(1977); M. Weizmann, etal, *Chemistry and Industry*, 402(1940); A. R. Katritzky and C. M. Marson, *J. Chem. Soc., Perkin II*, 1455(1983); 7-bromo-1-tetralone: L. F. Fieser and A. M. Seligman, *J. Amer. Chem. Soc.*, 60, 170(1938); 6-amino-1-tetralone: N. L. Allinger and E. S. Jones, supra.

For syntheses involving the Suzuki reaction, see A. Suzuki, et al, *Syn. Comm.*, 11, 513(1981); and related chemistry: Wiley, P. F., *J. Amer. Chem. Soc.*, 73, 4205(1951); Flemming, W., etal, *Chem. Ber.*, 58, 1612(1925); N. Miyaura, T. Yanagi, and A. Suzuki, *Syn. Comm.*, 11, 513(1981); V. Snieckus, etal, *J. Org. Chem.*, 56, 3763(1991); V. N. Kalinin, *Synthesis*, 413, (1992); V. Snieckus, etal, *Tet. Letters*, 29, 5459(1988); V. Snieckus and M. A. Siddiqui, ibid, 5463(1988).

For coupling to a known azetidinone to the side chain using Lewis acid catalysis, see, e.g., A. G. M. Barrett & P. Quayle, *J. Chem. Soc. Chem. Comm.* 1076(1981 ); Reider, P. J., et al. *Tet. Let.* 23, 2293 (1982); Hirai, K. et al. *Heterocycles* 17, 201 (1982); R. P. Attrill, A./G. M. Barrett, P. Quayle, J. Van der Westhuizen & M. J. Betts, *J. Org. Chem.* 49, 1679 (1984).

The synthesis, substitution and elaboration of dibenzofurans and dibenzothiophenes has been well reviewed in the literature: M. V. Sargent & P. O Stransky, *Adv. Heterocycl. Chem.* 35, 1–81 (1984); W. E. Parham *Heterocyclyl. Comp.*, 2, 123 (1951); R. Livingstone in *Rodd's Chemistry of Carbon Compounds*, 2d ed. Vol. IV Part A, *Heterocyclic Compounds*, 194–202 (1973); F. M. Dean and M. V. Sargent in *Comprehensive Heterocyclic Chemistry*, Vol. 4, Part 3, 599 (1979); J. Ashby & C. C. Cook, *Adv. Heterocycl. Comp.* 2, 164 (1951); R. Livingstone in *Rodd's Chemistry of Carbon Compounds*, 2d ed., Vol. IV, Part A, *Heterocyclic Compounds*, 300–305 (1973); S. Rajappa in *Comprehensive Heterocyclic Chemistry*, Vol. 4, Part 3, 741 (1979); E. Campaigne, ibid., 863 (1979).

Deblocking may be carried out in a conventional manner. For compounds prepared according to the Flow Sheets, deprotection of silicon based protecting groups may be carried out by using tetrabutylammonium fluoride and acetic acid in a tetrahydrofuran solution. For allyl derived protecting groups, the palladium catalyzed reaction, in a solution containing potassium 2-ethylhexanoate or, alternatively, another suitable nucleophile such as pyrrolidine or dimedone, may be employed.

The carbapenem compounds of the present invention are useful per se and in their pharmaceutically acceptable salt and ester forms in the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

The pharmaceutically acceptable salts referred to above may take the form —COOY. The Y may be an alkali metal cation such as sodium or potassium. Other pharmaceutically acceptable cations for Y may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above nay also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. These cationic salts serve as a counterion for the carboxylate anion.

The pharmaceutically acceptable esters of the present invention are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. The esters which are hydrolizable under physiological conditions are also referred to as "biolabile esters". Many biolabile esters have oral activity, protecting the drug from excessive acid degradation upon oral administration.

Some of the groups which Y represents form biolabile esters with the carboxylate to which Y is attached. Biolabile exters are biologically hydrolizable, and many are suitable for oral administration, due to good absorption through the stomach or intenstinal mucosa, resistance to gastric acid degradation and other factors. Examples of biolabile esters include compounds in which Y represents an alkoxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. All of these groups can be substituted in the alkyl or aryl portions thereof with acyl or halo groups. The following Y species are preferred as biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

Some of the novel carbapenem compounds of the present invention take the form COOY, where Y is a readily removable carboxyl protecting group. Such conventional groups consist of known groups which are used to protectively block the carboxyl group during the synthesis procedures described therein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation. Examples of such ester protecting groups include benzhydryl, p-nitrobenzyl, 2-naphthylmethyl, allyl, benzyl, trichloroethyl, silyl such as trimethylsilyl or trimethylsilylethyl, phenacyl, p-methoxybenzyl, acetonyl, o-nitrobenzyl, p-methoxyphenyl, 4-pyridylmethyl, and t-butyl.

Likewise, the hydroxy group at position 8 can be protected as appropriate to facilitate the syntheses described herein.

The compounds of the present invention are valuable antibacterial agents active against various Gram-positive and to a lesser extent Gram-negative bacteria, and accordingly find utility in human and veterinary, medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in compositions in concentrations ranging from about 0.01 to about 100 parts of antibiotic per million pans of solution in order to destroy or inhibit the growth of harmful bacteria on medical and dental equipment and as bactericides in industrial applications, for example in water based paints and in the white water of paper mills to inhibit the growth of harmful bacteria.

Many of compounds of the present invention are biologically active against MRSA/MRCNS. This is demonstrated below using the following biological activity protocol.

In vitro antibacterial activity determined in accordance with the protocol set forth below is predictive of in vivo activity, when the compounds are administered to a mammal infected with a susceptible bacterial organism.

Minimum inhibitory concentrations for different compounds may be calculated using the procedures set forth in Lorian, V. (ed.) *Antibiotics in Laboratory Medicine* (3rd ed.) pages 30–35 if desired. However, by comparing disc sensitivities to a known compound, e.g., imipenem, this calculation is not required to recognize MRSA/MRCNS activity.

Assay Used to Test the Activities of Carbapenems Against Methicillin-Resistant Staphylococci: The assay is an antibiotic disc-diffusion assay modeled after the method described by Bauer and Kirby, et al.1, with the following modifications and clarifications:

Agar: This assay employs an agar depth of 2 mm instead of 4 mm.

Zone Readings: The inner, compeltely clear zone is measured.

Culture Storage: Frozen vials of strains are stored at −80° C. Working slants are prepared from frozen vials and are used for 1 month to 6 weeks. For methicillin-resistant2 strains the slant medium is Muleller Hinton Agar; for control strains the slant medium is Brain Heart Infusion Agar. After inoculation from frozen vials, methicillin-resistant slant cultures are incubated at 28° C. until good growth is achieved (approximately 20 hours); slants of control strains are incubated at 37° C. for 16–18 hours.

Preparation of Control Inocula for Assay: Pipet 2 ml Brain Heart Infusion Broth (BHIB) into a sterile, plastic 17×100 mm tube. Use a sterile cotton tipped applicator to pick up a very small amount of culture from the slant and twirl it in the BHIB to achieve a light but visible inoculum (approximately $1 \times 10^6$–$10^7$ cuf/ml). Incubate at 37° C. and 220 rpm for 17–18 hours.

Preparation of Methicillin-Resistant Inocula for Assay: For methicillin-resistant strains, inoculate 0.5 ml of BHIB heavily (to achieve appromaitely $1 \times 10^8$–$10^9$ cfu/ml) from the slant culture by using a sterile cotton tipped applicator. With the applicator spread approximately 0.1 ml of the suspension onto the surface of a 15×100 mm petri plate containing 10 ml Mueller Hinton Agar. Incubate the plate at 30° C. for approximately 18 hours.

Inoculum Adjustment: The 17–18 hour control Staphylococci cultures are diluted 100× in phosphate-buffered saline (PBS).

Methicillin-resistant Staphylococci: With a cotton tipped applicator, swab enough growth off the grown plates into 1 ml BHIB to achieve a visual concentration of approximately $1 \times 10^9$ cfu/ml. Mix vigorously and dilute in PBS so that dilutions appear visually to be slightly more concentrated than the 100×diluted control cultures. Measure % transmission (% T) at 660 nm in a Spectronic 20 or other spectrophotometer. Add measured quantities of PBS to dilutions to achieve % T @ 1% above or below the % T measurement for the control cultures. Make sterile dilutions using the same proportions.

Plate Incubation Following Plate Inoculation and Disc Placement: Incubate control plates for 18 hours at 37° C. Incubate methicillin-resistant Staphylococci plates for 18 hours at 30° C.

The compounds of this invention may be used in a variety of pharmaceutical preparations. They may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, nay be prepared in unit dosage form in ampules, or in multidose containers. The injectable compositions may take such forms as suspensions, solutions, or emulsions in oily or aqueous vehicles, and may contain formulating agents. Alternatively, the active ingredient may be in powder (lyophillized or non-lyophillized) form for reconstitution at the time of delivery with a suitable vehicle, such as sterile water.

Topical applications may be formulated in hydrophobic or hydrophilic bases as ointments, creams, lotions, paints, or powders.

Oral compositions may take such forms as tablets, capsules, oral suspensions and oral solutions. The oral compositions may utilize conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ a dosage amount in the range of from about 250 mg to 1000 mg. In parenteral administration, the unit dosage will typically include the pure compound in sterile water solution or in the form of a soluble powder intended for solution, which can be adjusted to neutral pH and isotonic.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many occuring carbapenems are susceptible to attack by a renal enzyme known as dehydropeptidase (DHP). This attack or degradation may reduce the efficacy of the carbapenem antibacterial agent. The compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g.,[European Patent Application Nos. 79102616.4, filed Jul. 24, 1979 (Patent No. 0 007 614); and 82107174.3, filed Aug. 9, 1982 (Publication No. 0 072 014)1.

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples.

PREPARATIVE EXAMPLE 1

Preparation of Tetralone Derivative

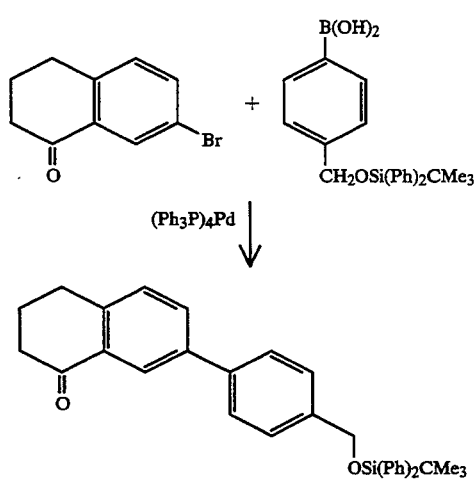

The 7-bromo-1-tetralone (2.07 g, 9.21 mmole), the boronic acid derivative(5.4 g, 13.8 mmole), from example tetrakistriphenylphosphinepalladium (531 mg, 0.46 mmole), and 8.4 mL (16.8 mmole) of a 2.0M aqueous solution of sodium carbonate were combined and stirred in 20 mL of toluene and 10mL of ethanol at reflux for 3 hour. The cooled mixture was partitioned between diethyl ether and water and the organic phase was separated, washed with brine, dried over anhydrous sodium sulfate, filtered, and evaporated. Purification by column chromatography on silica gel eluted with dichloromethane-pet. ether(1:1) gave 4.53 g (100%) of the product.

$^1$H NMR(CDCl$_3$)δ: 1.12(s,9H), 2.18(p,J=6 Hz, 2H), 2.71(t,J=6 Hz, 2H), 3.02(t,J=6 Hz, 2H), 7.32–7.76(m,16H), and 8.3(d,J=2 Hz, 1H).

PREPARATIVE EXAMPLE 2

Preparation of Tetralone Stannane

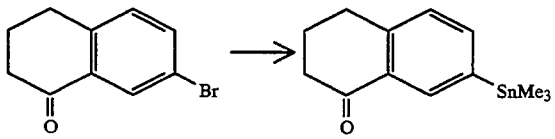

The 7-bromo-1-tetralone (225 mg, 1.0 mmole), 655.2 mg (2.0 mmole) of hexamethylditin, tetrakistriphenylphosphinepalladium (57.7 mg, 0.05 mmole), and 26.2 mg(0.1 mmole) of triphenylphosphine were combined and stirred in 3 mL of toluene at 100° C. for 1 hour. The cooled mixture was partitioned between ethyl acetate and ice-water and the organic phase was separated, washed with brine, dried over anhydrous sodium sulfate, filtered, and evaporated. Purification by plate-layer chromatography on silica gel eluted with dichloromethane-pet. ether(2:1) gave 307.2 mg (99%) of the stannane.

$^1$H NMR(CDCl$_3$) δ: 0.16–0.44(m,9H), 2.16(p, J=6 Hz, 2H), 2.69 (t, J=6 Hz, 2H), 2.95(t, J=6 Hz, 2H), 7.22(d, J=7.9 Hz, 1H), 7.6(dd, J=1.2 and 7.9 Hz, 1H), and 8.16(bs, 1H).

PREPARATIVE EXAMPLE 3

Preparation of Tetralone Derivative

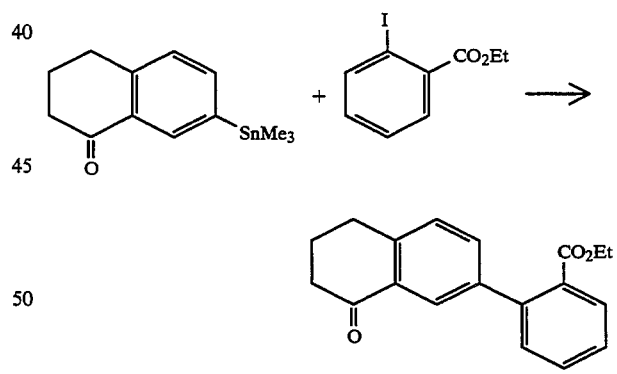

The 7-trimethylstannyl-1-tetralone (294.1 mg, 0.95 mmole), 262.8 mg(0.95 mmole) of ethyl-2-iodo-benzoate, 19.8 mg(0.02 mmole) trisdibenzylideneacetonedipalladium-chloroform catalyst and 144.5 mg(0.1 mmole) of diisopropylammonium hydrochloride were combined and stirred in 3 mL of N-methylpyrrolidinone at room temperature for 1.5 hour. The mixture was partitioned between diethyl ether and ice-water and the organic phase was separated, washed twice with water and then brine, dried over anhydrous sodium sulfate, filtered, and evaporated. Purification by plate-layer chromatography on silica gel eluted with dichloromethane-pet. ether(3:1) gave 214.7 mg(77%) of the coupled product.

$^1$H NMR(CDCl$_3$) δ: 1.11(t, J=7 Hz, 3H), 2.18(p, J=6 Hz, 2H), 2.65(t, J=6 Hz, 2H), 3.02(t, J=6 Hz, 2H), 4.14(q, J=7 Hz, 2H),7.29-7.54(m,5 H), 7.87(dd, J=1.9 and 6.7 Hz, 1H), and 8.0(d, J=1.9 Hz, 1H). IR(CH$_2$Cl$_2$)cm$^{-1}$: 1720 and 1683.

PREPARATIVE EXAMPLE 4

Preparation of Acid Tetralone Derivative

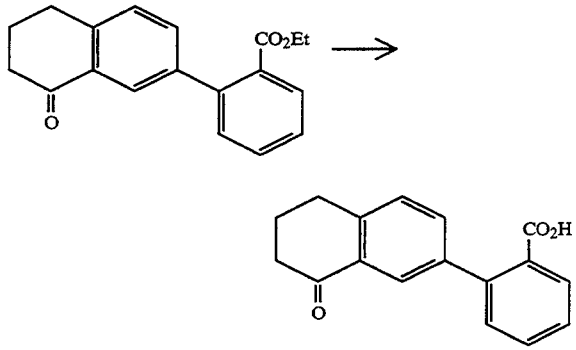

A stirred mixture of 197.6 mg (0.67 mmole) of the tetralone ester derivative and 282.1 μL (1.41 mmole) of 5N NaOH solution in 3 mL of methanol was stirred at ambient temperature for 16 hours, and then refluxed for 3 hours. The cooled mixture was concentrated in vacuo, diluted with water and extracted with ether. The separated aqueous layer was acidified with 2N HCl and extracted with ether. The extract was dried over anhydrous sodium sulfate, filtered, and evaporated to give 112 mg (63%) of the tetralone acid derivative as a colorless foam.

$^1$H NMR (CDCl$_3$) δ: 2.2 (p, J=6 Hz, 2H), 2.7 (t, J=6 Hz, 2H), 3.02 (t, J=6 Hz, 2H), 7.24–7.6 (m, 5H), 7.98 (m, 1H), and 8.04 (m, 1H).

PREPARATIVE EXAMPLE 5

Preparation of Cyclohexanonyl-fluoreneone Derivative

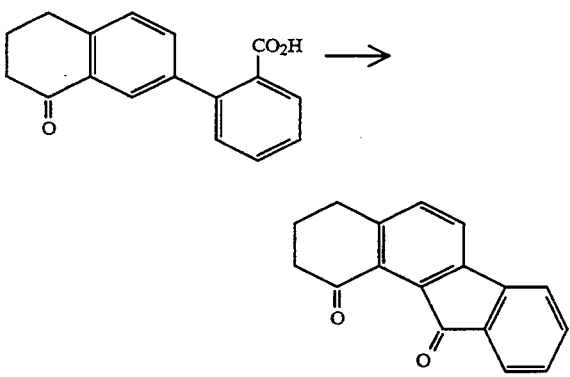

A stirred mixture of 107 mg (0.4 mmole) of the tetralone acid derivative and 1.5 g of polyphosphoric acid (PPA) in 3 mL of p-xylene was stirred at 130° C. for 0.5 hour. The mixture was cooled and the xylene decanted from the separated PPA phase. The PPA phase was dissolved in water and extracted with a mixture of ether and methylene chloride. The separated organic phase was washed with brine, dried over anhydrous sodium sulfate, filtered, and evaporated. The dark red solid was purified by preparative plate layer chromatography [one development methylene chloride] to give 41.6 mg (42%) of the product.

$^1$H NMR (CDCl$_3$) δ: 2.12 (p, J=6 Hz, 2H), 2.75 (t, J=6 Hz, 2H), 2.89 (t, J=6 Hz, 2H), 7.23-7.65 (m, 6H). IR (CH$_2$Cl$_2$)cm$^{-1}$: 1721 and 1690.

PREPARATIVE EXAMPLE 6

Preparation of 4-t-Butyldiphenylsiloxymethylbromobenzene

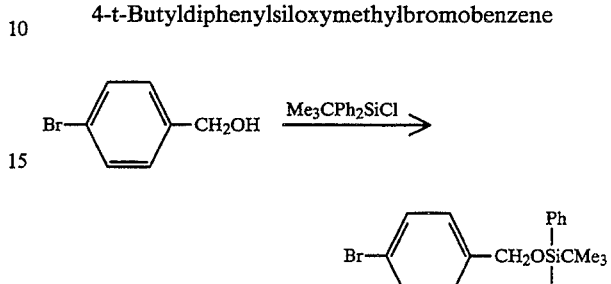

To a stirred solution of 7.48 g (40 mmoles) of p-bromobenzyl alcohol and 6.07 g (60 mmoles) of triethylamine in 70 mL of sieve dried DMF at 0° C. was added 14.3 g (52 mmoles) of neat t-butyldiphenylsilylchloride. The ice-water bath was removed and the mixture was stirred further for 20 hours.

The mixture was partitioned between ether, ice-water, and 2N hydrochloric acid, and the organic phase was separated, washed with water and brine, dried over anhydrous sodium sulfate, filtered, and evaporated.

Purification by column chromatography on 200 g of EM-60 silica gel eluting with hexanes-methylene chloride (3:1) gave 15.9 g (94%) of the title compound.

NMR (CDCl$_3$) δ: 1.1 (s, 9H), 4.72 (s, 2H), 7.22 (d, J=8.3 Hz, 2H), 7.43 (m, 8H), 7.7 (m, 4H).

PREPARATIVE EXAMPLE 7

Preparation of 4-t-butyldiphenylsiloxymethylphenylboronic acid

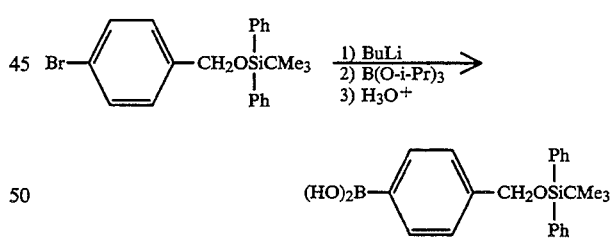

To a stirred solution of p-t-butylidiphenylsiloxymethylbromobenzene (10.1 g, 23.8 mmoles) in 100 mL of dry tetrahydrofuran at −78° C. under nitrogen was added dropwise 9.9 mL (25.0 mmoles) of 2.5M n-butyllithium in hexane. The mixture was stirred at −78° C. for 15 minutes and 4.7 g (25.0 mmoles) of triisopropylborate was added. After 5 minutes, the low temperature bath was removed, and the mixture was stirred further for 1.5 hours.

The mixture was poured onto ice-2N hydrochloric acid and ether was added. The biphasic mixture was stirred for 0.5 hour and the organic phase was separated, washed with brine, dried over anhydrous sodium sulfate, filtered, and evaporated to give 8.8 g (94.2% of crude product).

Precipitation from an ether-methylene chloride solution of the crude material with hexanes gave 7.1 g (76%) from two crops.

EXAMPLE 1

Preparation of Azetidinone 1

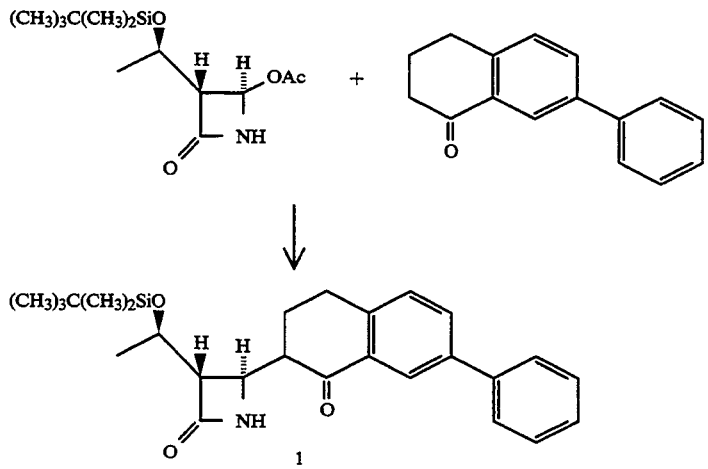

To a stirred mixture of 3.68 g(12.7 mmole) of azetidinone, 4.26 g(19 mmole) of 7-phenyltetralone, and 2.59 g(25.6 mmole) of triethylamine in 50 mL of sieve dried dichloromethane at 0° C. was added 6.26 g (28.1 mmole) of trimethylsilyl triflate. The resulting mixture was stirred under an inert atmosphere of nitrogen at 0° C. for four hours. The mixture was partitioned between diethyl ether, ice-water, and 2N hydrochloric acid. The organic phase was separated, washed with brine and then saturated sodium bicarbonate and sodium chloride, dried over anhydrous sodium sulfate, filtered, and evaporated.

The residue was purified by silica gel chromatography using toluene-diethyl ether(3:1) as eluant, to give 5.5 g(95%) of the product mixture 1. By a combination of crystallization and silica gel chromatography the individual α and β isomers were separated.

α-Isomer:
$^1$H NMR(CDCl$_3$) δ: 0.08(s, 3H), 0.1(s, 3H), 0.9(s, 9H), 1.3(d, 3H), 1.94(m), 2.34(m), 2.58(m), 2.86(m), 3.08(m), 3.76(dd, 1H), 4.22(p, 1H), 6.54(bs, 1H), 7.28–7.8(m, 7H), and 8.22(d, 1H). IR(CH$_2$Cl$_2$)cm$^{-1}$: 3420, 1755, 1660, and 1620. MS(m/e): 392[M+—C(CH$_3$)$_3$].

β-Isomer:
$^1$H NMR(CDCl$_3$) δ: 0.1 (s, 6H), 0.88(s, 9H), 1.28(d, 3H), 1.98–2.42(m, 2H), 2.76(m, 1H), 3.1(m, 3H), 4.3(p, 1H), 4.48(t, 1H), 5.96(bs, 1H), 7.3–7.8(m, 7H), and 8.22(d, 1H). IR(CH$_2$Cl$_2$)cm−1: 3410, 1760, 1660, and 1620. MS(m/e): 392[M+—C(CH$_3$)$_3$].

α and β isomers refer to the carbon atom attached to C-4 of the azetidinone ring.

EXAMPLE 1A

Preparation of Azetidinones

In a manner analogous to Example 1, the following azetidinones were prepared:

| | YIELDS (%) | $^1$H NMR SHIFT (δ) H-4 | |
|---|---|---|---|
| | | α-ISOMER | β-ISOMER |
| | 81 | 3.74 | 4.47 |
| | 72 | 3.72 | 4.46 |

| | YIELDS (%) | ¹H NMR SHIFT (δ) H-4 | |
|---|---|---|---|
| | | α-ISOMER | β-ISOMER |
| | 80 | 3.76 | 4.47 |
| | 47 | 3.70 | 4.28 |

PG = Si(Me)₂CMe₃

EXAMPLE 2

Synthesis of Oxalimide 2

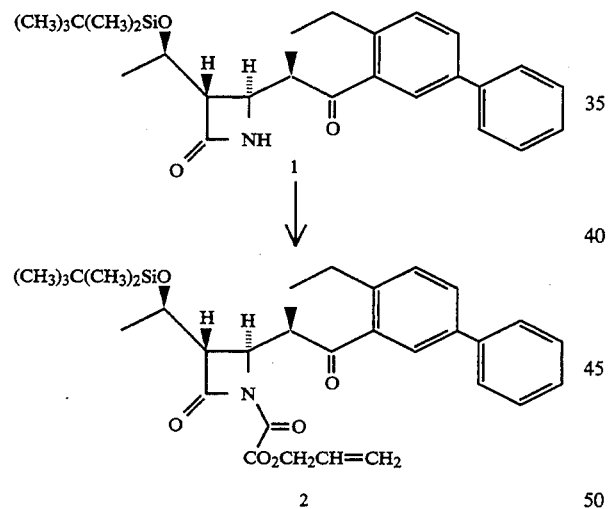

To a stirred solution of 449 mg(1 mmole) of β-isomeric azetidinone 1, from example 1, and 316.4 mg(4 mmole) of pyridine in 4 mL of sieve dried dichloromethane at 0° C. under an atmosphere of nitrogen was added 1.5 mL of a 2M stock solution of allylchlorooxalate in dichloromethane. The resulting mixture was stirred at 0° C. for 0.5 hour and then partitioned between diethyl ether, ice-water, and pH 7 phosphate buffer. The organic phase was separated, washed with brine, dried over anhydrous sodium sulfate, filtered, evaporated, and dried in vacuo to provide 568 mg of crystalline solid 2.

¹H NMR(CDCl₃) δ: 0.06(s, 6H), 0.85(s, 9H), 1.2(d, J=6.3 Hz, 3H), 2.0–2.3(m, 2H), 3.1–3.3(m, 4H), 4.3(m, 1H), 4.68(t, J=3.4 Hz, 1H), 4.8(m, 2H), 5.28–5.45(m, 2H), 5.9–5.99(m, 1H), 7.26–7.76(m, 7H), and 8.28(bs, 1H). IR(CH₂Cl₂)cm⁻¹: 1810, 1752, 1680, and 1620.

EXAMPLE 3

Synthesis of Phosphorane 3

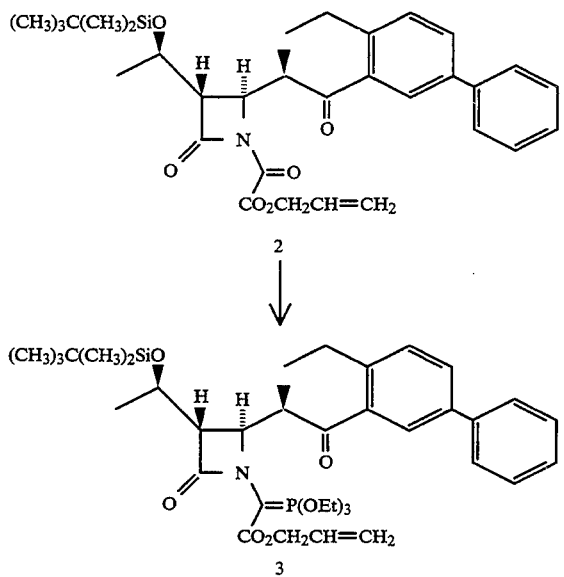

The oxalimide 2 (567.4 mg, 1 mmole), from example 2, and triethylphosphite(1.68 g, 10 mmole) in 5 mL p-xylene was stirred at 120° C. under an inert atmosphere of nitrogen for 1.5 hours. The cooled mixture was rotoevaporated under high vacuum and dried further in vacuo to provide a quantitative amount of phosphorane product 3, which was used immediately without further purification.

EXAMPLE 4

Preparation of Carbapenem 4

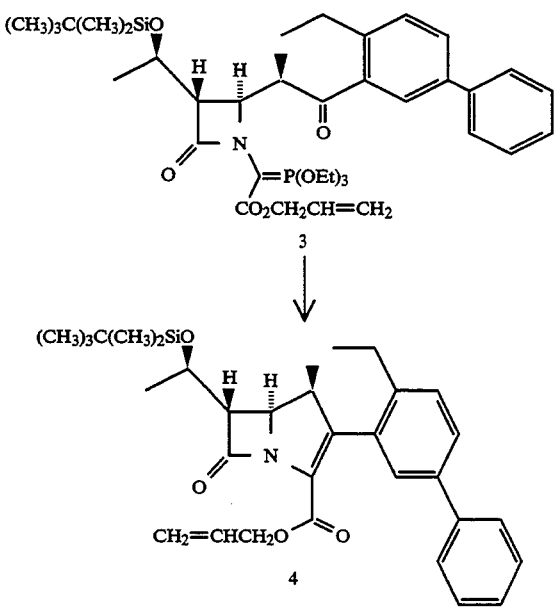

A stirred solution of phosphorane 3 (719.1 mg, 1 mmole), from Example 3, with a crystal of hydroquinone in 25 mL of p-xylene was kept at 140° C. under an atmosphere of nitrogen for 24 hours. The cooled solution was evaporated and the residue purified by plate layer chromatography [one development pet. ether-ether(3:1)] to give 353 mg(66%) of 4 as a yellow foam.

$^1$H NMR(CDCl$_3$) δ: 0.097(s, 6H), 0.9(s, 9H), 1.27(d, J=6.1 Hz, 3H), 1.94–2.1(m, 2H), 3.06–3.2(m, 3H), 3.25(dd, J=3.2 and 6.1 Hz, 1H), 4.3(m, 1H), 4.32(dd, J=3.2 and 7.5 Hz, 1H), 4.7(m, 2H), 5.1–5.42(m, 2H), 5.8–6.02(m, 1H), 7.16–7.6(m, 7H), and 8.0(d, J=1.5 Hz, 1H). IR(CH$_2$Cl$_2$)cm$^{-1}$: 1775 and 1718. UV(dioxane) nm: 326, 269. MS(m/e): 529(M+).

EXAMPLE 4A

Preparation of Carbapenems

Using the procedures of examples 2, 3, and 4, the following quadracyclic carbapenems were prepared:

| | OVERALL YIELD (%) | CYLIZATION TIME (HR) | $^1$H NMR SHIFT (δ) H-5 | H-8 |
|---|---|---|---|---|
| (structure 1) | 33 | 20 | 4.38 | 7.88 |
| (structure 2) | 19 | 22 | 4.30 | 7.72 |
| (structure 3) | 27 | 20 | 4.33 | 8.02 |

|  | OVERALL YIELD (%) | CYLIZATION TIME (HR) | $^1$H NMR SHIFT ($\delta$) H-5 | H-8 |
|---|---|---|---|---|
| (structure 1) | 28 | 96 | 3.81 | 8.79 |
| (structure 2) | 14 | 66 | 3.81 | 8.61 |
| (structure 3) | 7 | 70 | 3.74 | 8.34 |

PG = Si(Me)$_2$CMe$_3$

EXAMPLE 4B

Preparation of Carbapenems

Using the procedures of examples 2, 3, and 4, the following hexacyclic carbapenems are prepared:

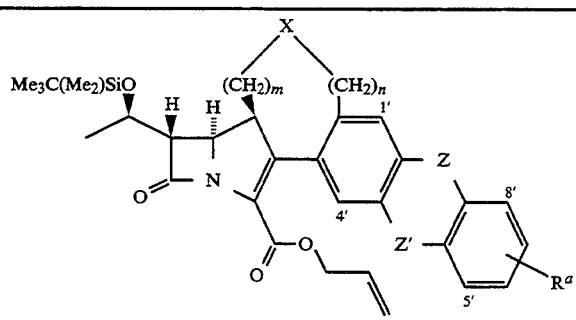

| m | n | X | Z | Z' | R$^a$ | Position R$^a$ |
|---|---|---|---|---|---|---|
| 1 | 1 | —C(O)NH— | C=O | bond | H | 1' |
| 2 | 1 | bond | C=O | bond | H | 1' |
| 1 | 1 | bond | S | bond | H | 1' |
| 1 | zero | O | S | bond | H | 1' |
| 1 | zero | S | S | bond | H | 1' |
| 1 | zero | SO$_2$ | SO$_2$ | bond | H | 1' |
| 1 | zero | C(OCH$_2$)$_2$ | S | bond | H | 1' |
| 1 | zero | NCO$_2$allyl | S | bond | H | 1' |
| 1 | zero | CH=CH | S | bond | H | 1' |
| 1 | 1 | —C(O)NH— | S | bond | H | 1' |
| 2 | 1 | bond | S | bond | H | 1' |
| 1 | 1 | bond | SO$_2$ | bond | H | 1' |
| 1 | zero | O | SO$_2$ | bond | H | 1' |
| 1 | zero | SO$_2$ | S | bond | H | 1' |

-continued

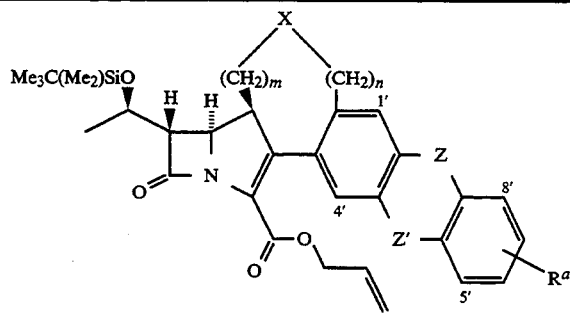

| m | n | X | Z | Z' | Rᵃ | Position Rᵃ |
|---|---|---|---|---|---|---|
| 1 | zero | —C(O)NH— | SO₂ | bond | H | 1' |
| 1 | zero | C(OCH₂)₂ | SO₂ | bond | H | 1' |
| 1 | zero | NCO₂allyl | SO₂ | bond | H | 1' |
| 1 | zero | CH=CH | SO₂ | bond | H | 1' |
| 1 | 1 | —C(O)NH— | SO | bond | H | 1' |
| 2 | 1 | bond | SO₂ | bond | H | 1' |
| 1 | 1 | bond | O | bond | H | 1' |
| 1 | zero | O | O | bond | H | 1' |
| 1 | zero | SO₂ | O | bond | H | 1' |
| 1 | zero | —C(O)NH— | O | bond | H | 1' |
| 1 | zero | C(OCH₂)₂ | O | bond | H | 1' |
| 1 | zero | NCO₂allyl | O | bond | H | 1' |
| 1 | zero | CH=CH | O | bond | H | 1' |
| 1 | 1 | —NHC=O | O | bond | H | 1' |
| 2 | 1 | bond | O—C=O | bond | H | 1' |
| 1 | 1 | bond | O—C=O | bond | H | 1' |
| 1 | zero | O | O—C=O | bond | H | 1' |
| 1 | zero | S | O—C=O | bond | H | 1' |
| 1 | zero | —C(O)NH— | O—C=O | bond | H | 1' |
| 1 | zero | C(OCH₂)₂ | O—C=O | bond | H | 1' |
| 1 | zero | NCO₂allyl | O—C=O | bond | H | 1' |
| 1 | zero | CH=CH | O—C=O | bond | H | 1' |
| 1 | 1 | bond | C=O | bond | CN | 1' |
| 1 | 1 | bond | C=O | bond | SCH₃ | 1' |
| 1 | 1 | bond | C=O | bond | SO₂CH₃ | 1' |
| 1 | zero | O | C=O | bond | CN | 1' |
| 1 | zero | S | C=O | bond | CN | 1' |
| 1 | zero | SO₂ | C=O | bond | H | 1' |
| 1 | zero | C(OCH₂)₂ | C=O | bond | H | 1' |
| 1 | zero | NCO₂allyl | C=O | bond | H | 1' |
| 1 | zero | CH=CH | C=O | bond | H | 1' |
| 1 | 1 | bond | C=O | bond | CHO | 7' |
| 1 | 1 | bond | C=O | bond | CF₃ | 8' |
| 1 | 1 | bond | C=O | bond | OCH₃ | 6' |
| 1 | zero | O | C=O | bond | SO₂NMe₂ | 1' |
| 1 | zero | S | C=O | bond | Cl | 1' |
| 1 | zero | SO₂ | C=O | bond | NHCHO | 1' |
| 1 | zero | C(OCH₂)₂ | C=O | bond | CO₂CH₃ | 1' |
| 1 | zero | NCO₂allyl | C=O | bond | SCF₃ | 1' |
| 1 | zero | CH=CH | C=O | bond | C(O)NMe₂ | 1' |
| 1 | 1 | —C(O)NH— | —C(O)— | bond | OC(O)CH₃ | 1' |
| 2 | 1 | bond | —C(O)— | bond | NHC(O)CH₃ | 1' |
| 1 | 1 | bond | S | bond | NHSO₂Me | 1' |
| 1 | zero | O | S | bond | CH₃ | 1' |
| 1 | zero | S | S | bond | CONH₂ | 1' |
| 1 | zero | SO₂ | SO₂ | bond | CN | 1' |
| 1 | zero | C(OCH₂)₂ | S | bond | C(O)Me | 1' |
| 1 | zero | NCO₂allyl | S | bond | C(S)NMe₂ | 1' |
| 1 | zero | CH=CH | S | bond | SCF₃ | 1' |
| 1 | 1 | —(O)CNH— | S | bond | CH₂CH₃ | 8' |
| 2 | 1 | bond | S | bond | CN | 8' |
| 1 | 1 | bond | SO₂ | bond | CHO | 8' |
| 1 | zero | O | SO₂ | bond | SCN | 8' |
| 1 | zero | SO₂ | S | bond | OC(O)NMe₂ | 8' |
| 1 | zero | —C(O)NH— | SO₂ | bond | CH₃ | 8' |
| 1 | zero | C(OCH₂)₂ | SO₂ | bond | CF₃ | 8' |
| 1 | zero | NCO₂allyl | SO₂ | bond | NHCO₂Me | 8' |
| 1 | zero | CH=CH | SO₂ | bond | Cl | 8' |
| 1 | 1 | —C(O)NH— | SO | bond | N₃ | 7' |
| 2 | 1 | bond | SO₂ | bond | —C(Me)=NOH | 7' |

-continued

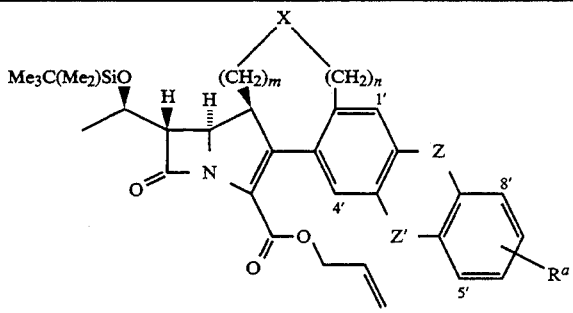

| m | n | X | Z | Z' | R^a | Position R^a |
|---|---|---|---|---|---|---|
| 1 | 1 | bond | O | bond | cyclohexyl | 7' |
| 1 | zero | O | O | bond | $C(O)NMe_2$ | 7' |
| 1 | zero | $SO_2$ | O | bond | CON(OH)Me | 7' |
| 1 | zero | —C(O)NH— | O | bond | $SO_2Me$ | 7' |
| 1 | zero | $C(OCH_2)_2$ | O | bond | CN | 7' |
| 1 | zero | $NCO_2$allyl | O | bond | F | 7' |
| 1 | zero | CH=CH | O | bond | $CO_2Et$ | 7' |
| 1 | 1 | —NHC(O)— | O | bond | $CF_3$ | 6' |
| 2 | 1 | bond | O—C=O | bond | $CH_3$ | 6' |
| 1 | 1 | bond | O—C=O | bond | $CH_2CN$ | 6' |
| 1 | zero | O | O—C=O | bond | $SCH_2CH_2CN$ | 6' |
| 1 | zero | S | O—C=O | bond | CN | 6' |
| 1 | zero | —C(O)NH— | O—C=O | bond | OMe | 6' |
| 1 | zero | $C(OCH_2)_2$ | O—C=O | bond | $NHC(O)CH_3$ | 6' |
| 1 | zero | $NCO_2$allyl | O—C=O | bond | F | 6' |
| 1 | zero | CH=CH | O—C=O | bond | $C(O)NH_2$ | 6' |

EXAMPLE 5

Preparation of Carbapenem 5

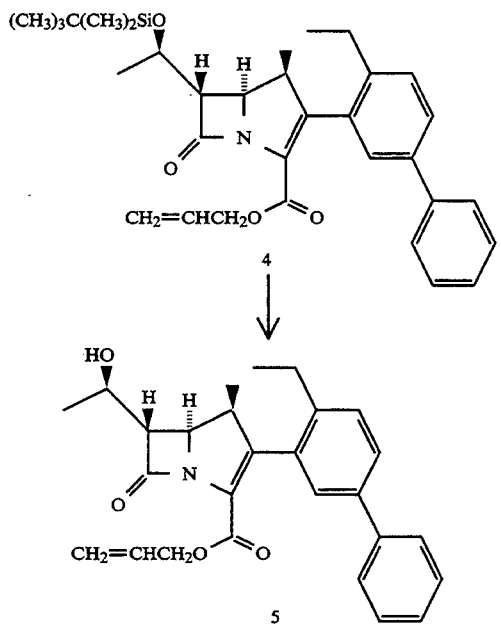

To a stirred solution of 4 (98.7 mg, 0.19 mmole) in 1 mL of tetrahydrofuran at room temperature under an atmosphere of nitrogen was added sequentially neat glacial acetic acid (39.2 mg, 0.65 mmole) and 0.56 mL(0.56 mmole) of a 1M solution of tetrabutylammonium fluoride in THF. The mixture was stirred at ambient temperature for 24 hours.

The mixture was partitioned between ethyl acetate, ice-water, and saturated sodium bicarbonate solution and the organic phase was separated, washed with brine, dried over anhydrous sodium sulfate, filtered, and evaporated.

Purification by plate layer chromatography [one development $CH_2Cl_2$-ether(3:1)] gave 45.1 mg(58%) of product 5.

$^1$H NMR(CDCl$_3$) δ: 1.36(d, J=6.2 Hz, 3H), 1.94–2.2(m, 3H), 3.08–3.28(m, 3H), 3.33(dd, J=3.2 and 6.6 Hz, 1H), 4.28(m, 1H), 4.36(dd, J=3.2 and 7.5 Hz, 1H), 4.7(m, 2H), 5.1–5.4(m, 2H), 5.8–6.02(m, 1H), 7.12–7.6(m, 7H), and 8.0(d, J=1.5 Hz, 1H). IR(CH$_2$Cl$_2$)cm$^{-1}$: 3600, 1775 and 1720. UV(dioxane) nm: 326, 254. MS(m/e): 415(M+).

EXAMPLE 5A

Preparation of Carbapenems

Following the procedure of example 5, the following quadracyclic carbapenems were prepared:

| | YIELD (%) | ¹H NMR SHIFT (δ) | |
|---|---|---|---|
| | | H-5 | H-8 |
| [structure 1] | 43 | 4.37 | 7.89 |
| [structure 2] | 53 | 4.34 | 7.72 |
| [structure 3] | 28 | 4.37 | 8.03 |
| [structure 4] | 53 | 3.85 | 8.72 |
| [structure 5] | 61 | 3.84 | 8.57 |

EXAMPLE 5B

Preparation of Carbapenems

Using the procedure of Example 5, the following hexacyclic carbapenems are prepared:

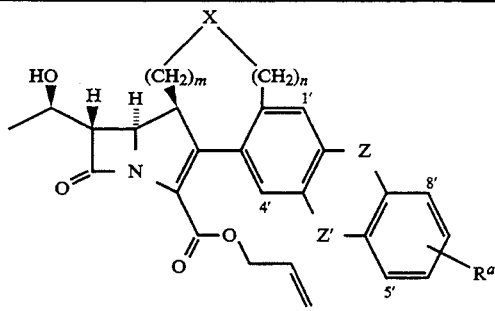

| m | n | X | Z | Z' | R$^a$ | Position R$^a$ |
|---|---|---|---|---|---|---|
| 1 | 1 | —C(O)NH— | C=O | bond | H | 1' |
| 2 | 1 | bond | C=O | bond | H | 1' |
| 1 | 1 | bond | S | bond | H | 1' |
| 1 | zero | O | S | bond | H | 1' |
| 1 | zero | S | S | bond | H | 1' |
| 1 | zero | SO$_2$ | SO$_2$ | bond | H | 1' |
| 1 | zero | C(OCH$_2$)$_2$ | S | bond | H | 1' |
| 1 | 1 | —C(O)NH— | S | bond | H | 1' |
| 2 | 1 | bond | S | bond | H | 1' |
| 1 | 1 | bond | SO$_2$ | bond | H | 1' |
| 1 | zero | O | SO$_2$ | bond | H | 1' |
| 1 | zero | SO$_2$ | S | bond | H | 1' |
| 1 | zero | —C(O)NH— | SO$_2$ | bond | H | 1' |
| 1 | zero | C(OCH$_2$)$_2$ | SO$_2$ | bond | H | 1' |
| 1 | zero | NCO$_2$allyl | SO$_2$ | bond | H | 1' |
| 1 | zero | CH=CH | SO$_2$ | bond | H | 1' |
| 1 | 1 | —C(O)NH— | SO | bond | H | 1' |
| 2 | 1 | bond | SO$_2$ | bond | H | 1' |
| 1 | 1 | bond | O | bond | H | 1' |
| 1 | zero | O | O | bond | H | 1' |
| 1 | zero | SO$_2$ | O | bond | H | 1' |
| 1 | zero | —C(O)NH— | O | bond | H | 1' |
| 1 | zero | C(OCH$_2$)$_2$ | O | bond | H | 1' |
| 1 | zero | NCO$_2$allyl | O | bond | H | 1' |
| 1 | zero | CH=CH | O | bond | H | 1' |
| 1 | 1 | —NHC=O | O | bond | H | 1' |
| 2 | 1 | bond | O—C=O | bond | H | 1' |
| 1 | 1 | bond | O—C=O | bond | H | 1' |
| 1 | zero | O | O—C=O | bond | H | 1' |
| 1 | zero | S | O—C=O | bond | H | 1' |
| 1 | zero | —C(O)NH— | O—C=O | bond | H | 1' |
| 1 | zero | C(OCH$_2$)$_2$ | O—C=O | bond | H | 1' |
| 1 | zero | NCO$_2$allyl | O—C=O | bond | H | 1' |
| 1 | zero | CH=CH | O—C=O | bond | H | 1' |
| 1 | 1 | bond | C=O | bond | CN | 1' |
| 1 | 1 | bond | C=O | bond | SCH$_3$ | 1' |
| 1 | 1 | bond | C=O | bond | SO$_2$CH$_3$ | 1' |
| 1 | zero | O | C=O | bond | CN | 1' |
| 1 | zero | S | C=O | bond | CN | 1' |
| 1 | zero | SO$_2$ | C=O | bond | H | 1' |
| 1 | zero | C(OCH$_2$)$_2$ | C=O | bond | H | 1' |
| 1 | zero | NCO$_2$allyl | C=O | bond | H | 1' |
| 1 | zero | CH=CH | C=O | bond | H | 1' |
| 1 | 1 | bond | C=O | bond | CHO | 7' |
| 1 | 1 | bond | C=O | bond | CF$_3$ | 8' |
| 1 | 1 | bond | C=O | bond | OCH$_3$ | 6' |
| 1 | zero | O | C=O | bond | SO$_2$NMe$_2$ | 1' |
| 1 | zero | S | C=O | bond | Cl | 1' |
| 1 | zero | SO$_2$ | C=O | bond | NHCHO | 1' |
| 1 | zero | C(OCH$_2$)$_2$ | C=O | bond | CO$_2$CH$_3$ | 1' |
| 1 | zero | NCO$_2$allyl | C=O | bond | SCF$_3$ | 1' |
| 1 | zero | CH=CH | C=O | bond | C(O)NMe$_2$ | 1' |
| 1 | 1 | —C(O)NH— | —C(O)— | bond | OC(O)CH$_3$ | 1' |
| 2 | 1 | bond | —C(O)— | bond | NHC(O)CH$_3$ | 1' |
| 1 | 1 | bond | S | bond | NHSO$_2$Me | 1' |
| 1 | zero | O | S | bond | CH$_3$ | 1' |
| 1 | zero | S | S | bond | CONH$_2$ | 1' |
| 1 | zero | SO$_2$ | SO$_2$ | bond | CN | 1' |
| 1 | zero | C(OCH$_2$)$_2$ | S | bond | C(O)Me | 1' |
| 1 | zero | NCO$_2$allyl | S | bond | C(S)NMe$_2$ | 1' |
| 1 | zero | CH=CH | S | bond | SCF$_3$ | 1' |
| 1 | 1 | —(O)CNH— | S | bond | CH$_2$CH$_3$ | 8' |
| 2 | 1 | bond | S | bond | CN | 8' |
| 1 | 1 | bond | SO$_2$ | bond | CHO | 8' |
| 1 | zero | O | SO$_2$ | bond | SCN | 8' |

-continued

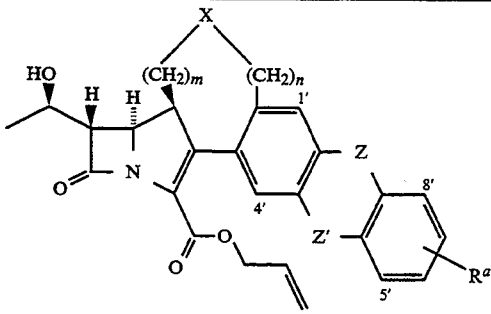

| m | n | X | Z | Z' | R$^a$ | Position R$^a$ |
|---|---|---|---|---|---|---|
| 1 | zero | SO$_2$ | S | bond | OC(O)NMe$_2$ | 8' |
| 1 | zero | —C(O)NH— | SO$_2$ | bond | CH$_3$ | 8' |
| 1 | zero | C(OCH$_2$)$_2$ | SO$_2$ | bond | CF$_3$ | 8' |
| 1 | zero | NCO$_2$allyl | SO$_2$ | bond | NHCO$_2$Me | 8' |
| 1 | zero | CH=CH | SO$_2$ | bond | Cl | 8' |
| 1 | 1 | —C(O)NH— | SO | bond | N$_3$ | 7' |
| 2 | 1 | bond | SO$_2$ | bond | —C(Me)=NOH | 7' |
| 1 | 1 | bond | O | bond | cyclohexyl | 7' |
| 1 | zero | O | O | bond | C(O)NMe$_2$ | 7' |
| 1 | zero | SO$_2$ | O | bond | CON(OH)Me | 7' |
| 1 | zero | —C(O)NH— | O | bond | SO$_2$Me | 7' |
| 1 | zero | C(OCH$_2$)$_2$ | O | bond | CN | 7' |
| 1 | zero | NCO$_2$allyl | O | bond | F | 7' |
| 1 | zero | CH=CH | O | bond | CO$_2$Et | 7' |
| 1 | 1 | —NHC(O)— | O | bond | CF$_3$ | 6' |
| 2 | 1 | bond | O—C=O | bond | CH$_3$ | 6' |
| 1 | 1 | bond | O—C=O | bond | CH$_2$CN | 6' |
| 1 | zero | O | O—C=O | bond | SCH$_2$CH$_2$CN | 6' |
| 1 | zero | S | O—C=O | bond | CN | 6' |
| 1 | zero | —C(O)NH— | O—C=O | bond | OMe | 6' |
| 1 | zero | C(OCH$_2$)$_2$ | O—C=O | bond | NHC(O)CH$_3$ | 6' |
| 1 | zero | NCO$_2$allyl | O—C=O | bond | F | 6' |
| 1 | zero | CH=CH | O—C=O | bond | C(O)NH$_2$ | 6' |

EXAMPLE 6

Preparation of Carbapenem 6

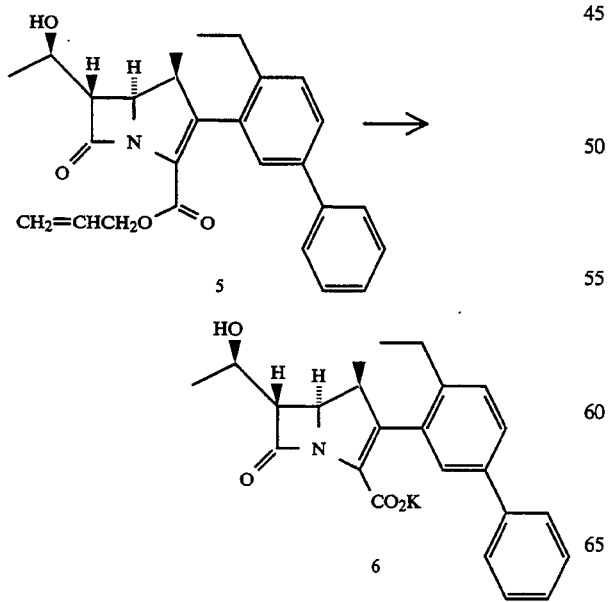

The carbapenem 5 (48.7 mg, 0.117 mmole), triphenylphosphine (9.2 mg, 0.035 mmole), tetrakistriphenylphosphine-palladium (13.5 mg, 0.018 mmole) and 0.26 mL(0.13 mmole)of a 0.5M solution of potassium-2-ethylhexanoate in ethyl acetate were combined and stirred in 2 mL of dichloromethane-ethyl acetate(1:1) at 0° C. for 0.5 hour. Diethyl ether was added to precipitate the crude product which was collected by centrifugation; decanted the supernatant, washed analogously with ether, and dried in vacuo to give 40 mg. Purification by reverse phase plate layer chromatography [one development water-acetonitrile(3:1)] gave after extraction of the UV active product band with acetonitrile-water(4:1), concentration, and lyophilization 10.8 mg(22%) of carbapenem 6.

$^1$H NMR(D$_2$O-CD$_3$CN, 2:1) δ: 1.57(d, J=6.3 Hz, 3H), 2.07–2.44(m), 2.95–3.82(m), 4.45–4.71(m, 2H), 4.79(HDO), 7.52–8.12(m, 7H), and 8.18(bs). IR(nujol)cm$^{-1}$: 1740 and 1600. UV(water) nm: 305, 257.

EXAMPLE 6A

Preparation of Carbapenems

Following the procedure of example 6, the following quadracyclic carbapenems were prepared:

| | YIELD (%) | UV:λ_max (nm) |
|---|---|---|
| (structure 1) | 30 | 321, 246 |
| (structure 2) | 44 | 304, 237 |
| (structure 3) | 49 | 305, 254 |
| (structure 4) | 50 | 324, 243 |

EXAMPLE 6B

Preparation of Carbapenems

Using the procedure of example 6, the following hexacyclic carbapenems are prepared:

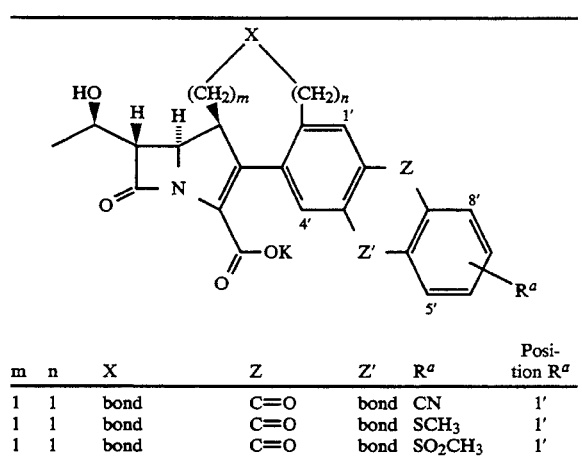

| m | n | X | Z | Z' | $R^a$ | Position $R^a$ |
|---|---|---|---|---|---|---|
| 1 | 1 | bond | C=O | bond | CN | 1' |
| 1 | 1 | bond | C=O | bond | $SCH_3$ | 1' |
| 1 | 1 | bond | C=O | bond | $SO_2CH_3$ | 1' |
| 1 | zero | O | C=O | bond | CN | 1' |
| 1 | zero | S | C=O | bond | CN | 1' |
| 1 | zero | $SO_2$ | C=O | bond | H | 1' |

-continued

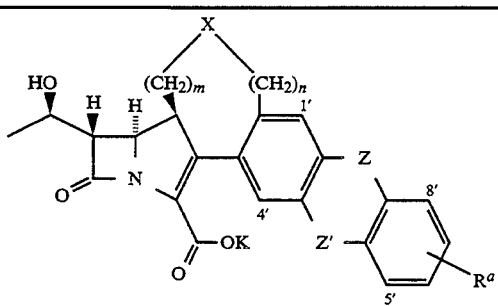

| m | n | X | Z | Z' | $R^a$ | Position $R^a$ |
|---|---|---|---|---|---|---|
| 1 | zero | $C(OCH_2)_2$ | C=O | bond | H | 1' |
| 1 | zero | NH | C=O | bond | H | 1' |
| 1 | zero | CH=CH | C=O | bond | H | 1' |
| 1 | 1 | O=C—NH— | C=O | bond | H | 1' |
| 2 | 1 | bond | C=O | bond | H | 1' |
| 1 | 1 | bond | S | bond | H | 1' |
| 1 | zero | O | S | bond | H | 1' |
| 1 | zero | S | S | bond | H | 1' |
| 1 | zero | $SO_2$ | $SO_2$ | bond | H | 1' |
| 1 | zero | $C(OCH_2)_2$ | S | bond | H | 1' |
| 1 | zero | NH | S | bond | H | 1' |
| 1 | zero | CH=CH | S | bond | H | 1' |
| 1 | 1 | O=C—NH— | S | bond | H | 1' |

-continued

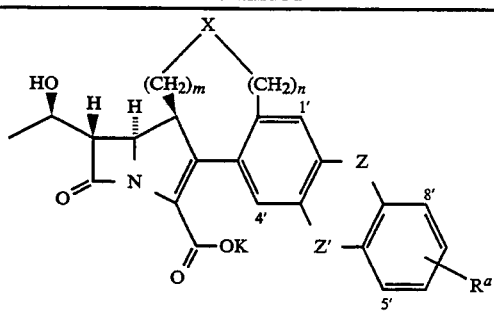

| m | n | X | Z | Z' | R$^a$ | Position R$^a$ |
|---|---|---|---|---|---|---|
| 2 | 1 | bond | S | bond | H | 1' |
| 1 | 1 | bond | SO$_2$ | bond | H | 1' |
| 1 | zero | O | SO$_2$ | bond | H | 1' |
| 1 | zero | SO$_2$ | S | bond | H | 1' |
| 1 | zero | O=C—NH— | SO$_2$ | bond | H | 1' |
| 1 | zero | C(OCH$_2$)$_2$ | SO$_2$ | bond | H | 1' |
| 1 | zero | NH | SO$_2$ | bond | H | 1' |
| 1 | zero | CH=CH | SO$_2$ | bond | H | 1' |
| 1 | 1 | O=C—NH— | SO | bond | H | 1' |
| 2 | 1 | bond | SO$_2$ | bond | H | 1' |
| 1 | 1 | bond | O | bond | H | 1' |
| 1 | zero | O | O | bond | H | 1' |
| 1 | zero | SO$_2$ | O | bond | H | 1' |
| 1 | zero | O=C—NH— | O | bond | H | 1' |
| 1 | zero | C(OCH$_2$)$_2$ | O | bond | H | 1' |
| 1 | zero | NH | O | bond | H | 1' |
| 1 | zero | CH=CH | O | bond | H | 1' |
| 1 | 1 | —NHC=O | O | bond | H | 1' |
| 2 | 1 | bond | O—C=O | bond | H | 1' |
| 1 | 1 | bond | O—C=O | bond | H | 1' |
| 1 | zero | O | O—C=O | bond | H | 1' |
| 1 | zero | S | O—C=O | bond | H | 1' |
| 1 | zero | O=C—NH— | O—C=O | bond | H | 1' |
| 1 | zero | C(OCH$_2$)$_2$ | O—C=O | bond | H | 1' |
| 1 | zero | NH | O—C=O | bond | H | 1' |
| 1 | zero | CH=CH | O—C=O | bond | H | 1' |

What is claimed is:
1. A compound represented by formula I:

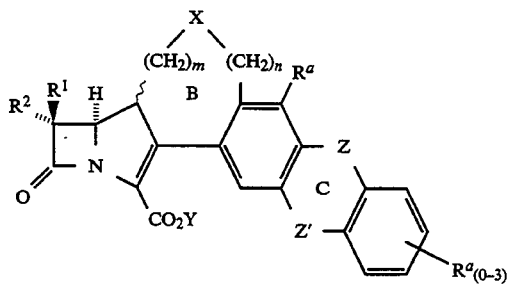

wherein:
m is an integer 0, 1, 2, 3, 4 or 5;
n is an integer 0, 1, 2, 3 or 4;
X represents (a) a bond; (b) —O—; (c) —S(O)$_x$— with x equal to 0, 1 or 2: (d) —C(O)—; (e) —NR'—; (f) —CH=CH—; (g) —C(O)NR'—; (h) —NR'C(O)—; (i) —CO$_2$—; (j) —OC(O)—; (k) —SO$_2$NR'— or (l) —NR'SO$_2$— with R' representing H, C$_1$ to C$_4$ alkyl or acetyl;
the values of m, n and X being selected such that ring B constitutes a 6 to 10 membered ring;
Y represents H, a pharmaceutically acceptable ester forming group, a carboxylate protecting group or a metal cation:
R$^1$ and R$^2$ independently represent H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$— or (CH$_3$)$_2$CF—:

one of Z and Z' represents a bond and the other represents a member selected from the group consisting of: —CH=CH—, —C(O)NR$^f$—, —NR$^f$C(O)—, —S(O)$_x$NR$^f$13, —NR$^f$S(O)$_x$—, —C(O)—, —OC(O)—, —C(O)O—, —O—, —S(O)$_x$— with x equal to 0, 1 or 2, or —NR$^f$— with R$^f$ representing H, C$_1$ to C$_4$ alkyl, —C(O)—C1-4 alkyl or —C(O)—C1-4 alkyl substituted with R$^q$, such that ring C is a 5 or 6 membered ring;

R$^q$ is a member of the group consisting of —OH, —OCH$_3$, —CN, —F, —CF$_3$ and —CO$_2$M$^a$ with M$^a$ representing H, alkali metal or methyl;

each R$^a$ independently represents hydrogen or a member selected from the group consisting of:
a) trifluoromethyl group which is —CF$_3$;
b) a halogen atom selected from the group consisting of —Br, —Cl, —F, or —I;
c) C$_1$-C$_4$ alkoxy radical which is —OC$_{1-4}$ alkyl, wherein the alkyl is optionally mono-substituted by R$^q$, where R$^q$ is as defined above;
d) a hydroxy group which is —OH;
e) a carbonyloxy radical which is —OC(O)R$^s$, where R$^s$ is C$_{1-4}$ alkyl or phenyl, each of which is optionally mono-substituted by R$^q$ as defined above;
f) a carbamoyloxy radical which is —OC(O)N(R$^y$)R$^z$, where R$^y$ and R$^z$ are independently H, C$_{1-4}$ alkyl, (optionally mono-substituted by R$^q$ as defined above), or are taken together to represent a 3- to 5-membered alkylidene radical which forms a ring (optionally substituted with R$^q$ as defined above), or a 2- to 4-membered alkylidene radical interrupted by —O—, —S—, —S(O)— or —S(O)$_2$— which forms a ring, said ring being optionally mono-substituted with R$^q$ as defined above;
g) a sulfur radical which is —S(O)$_n$—R$^s$, where n=0–2, and R$^s$ is defined above;
h) a sulfamoyl group which is —SO$_2$N(R$^y$)R$^z$, where R$^y$ and R$^z$ are as defined above;
i) azido which is N$_3$
j) a formamido group which is —N(R$^t$)C(O)H, where R$^t$ is H or C$_{1-4}$ alkyl, said alkyl group being optionally mono-substituted with R$^q$ as defined above;
k) an alkylcarbonylamino radical which is —N(R$^t$)C(O)C$_{1-4}$ alkyl, wherein R$^t$ is as defined above;
l) an alkoxycarbonylamino radical which is —N(R$^t$)C(O)OC$_{1-4}$ alkyl, where R$^t$ is as defined above;
m) a ureido group which is —N(R$^t$)C(O)N(R$^y$)R$^z$ where R$^t$, R$^y$ and R$^z$ are defined above;
n) a sulfonamido group which is —N(R$^t$)SO$_2$R$^s$, where R$^s$ and R$^t$ are as defined above;
o) a cyano group which is —CN;
p) a formyl or acetalized formyl radical which is —C(O)H or —CH(OCH$_3$)$_2$;
q) an alkylcarbonyl radical wherein the carbonyl is acetalized: —C(OCH$_3$)$_2$C$_1$-C$_4$ alkyl, where the alkyl is optionally mono-substituted by R$^q$ as defined above;

r) a carbonyl radical which is —C(O)R$^s$, where R$^s$ is as defined above;

s) a hydroximinomethyl radical in which the oxygen or carbon atom is optionally substituted by a C$_1$-C$_4$ alkyl group which is —(C=NOR$^z$)R$^y$ where R$^y$ and R$^z$ are as defined above, except they may not be joined together to form a ring;

t) an alkoxycarbonyl radical which is —C(O)OC$_{1-4}$alkyl, where the alkyl is optionally mono-substituted by R$^q$ as defined above;

u) a carbamoyl radical which is —C(O)N(R$^y$)R$^z$, where R$^y$ and R$^z$ are as defined above;

v) an N-hydroxycarbamoyl or N(C$_1$-C$_4$ alkoxy)-carbamoyl radical in which the nitrogen atom may be additionally substituted by a C$_1$-C$_4$ alkyl group: —C(O)N(OR$^y$)R$^z$, where R$^y$ and R$^z$ are as defined above, except they may not be joined together to form a ring;

w) a thiocarbamoyl group: —C(S)N(R$^y$)R$^z$ where R$^y$ and R$^z$ are as defined above;

x) carboxyl which is —COOM$^a$ where M$^a$ is as defined above;

y) thiocyanate which is —SCN;

z) trifluoromethylthio which is —SCF$_3$;

aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;

ab) an anionic function selected from the group consisting of: phosphono [P=O(OM$^a$)$_2$]; alkylphosphono {P=O(OM$^a$)-[O(C$_1$-C$_4$ alkyl)]}; alkylphosphinyl [P=O(OM$^a$)-(C$_1$-C$_4$alkyl)]; phosphoramido [P=O(OM$^a$)N(R$^y$)R$^z$ and P=O(OM$^a$)NHR$^x$]; sulfino (SO$_2$M$^a$); sulfo (SO$_3$M$^a$); acylsulfonamides selected from the structures SO$_2$NM$^a$CON(R$^y$)R$^z$; and SO$_2$N-M$^a$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, said R$^q$, M$^a$, R$^y$ and R$^z$ being as defined above;

ac) a C$_5$-C$_7$ cycloalkyl group in which one of the carbon atoms in the ring is replaced by a heteroatom selected from O, S, NH, or N(C$_1$-C$_4$ alkyl) and in which one additional carbon may be replaced by the NH or N(C$_1$-C$_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) a C$_2$-C$_4$ alkenyl radical, optionally mono-substituted by one of the substituents a) to ac) above and phenyl which is optionally substituted by R$^q$ as defined above;

ae) a C$_2$-C$_4$ alkynyl radical, optionally mono-substituted by one of the substituents a) to ac) above;

af) a C$_1$-C$_4$ alkyl radical;

ag) a C$_1$-C$_4$ alkyl group mono-substituted by one of the substituents a)-ac) above;

ah) a 2-oxazolidinonyl moiety in which the point of attachment is the nitrogen atom of the oxazolidinone ring, the ring oxygen atom is optionally optionally replaced by a heteroatom selected from S and NR$^t$ (where R$^t$ is as defined above) and one of the saturated carbon atoms of the oxazolidinone ring is optionally mono-substituted by one of the substituents a) to ag) above, or the pharmaceutically acceptable salts thereof.

2. The compound of claim 1, wherein R$^1$ is hydrogen and R$^2$ is (R)CH$_3$CH(OH)— or (R)CH$_3$CH(F)—.

3. The compound according to claim 1 in which Z represents a carbonyl —C(O)—.

4. The compound according to claim 1 wherein Z represents —O—.

5. The compound of claim 1, wherein R$^a$ is selected from:

| | |
|---|---|
| —OCH$_3$ | |
| —OCH$_2$CH$_2$OH | —OCH$_2$CO$_2$Me |
| —F | —CF$_3$ |
| —Br | —Cl |
| —OH | —I |
| —OC(O)NH$_2$ | —OC(O)CH$_3$ |
| —S(O)CH$_3$ | —SCH$_3$ |
| —SCH$_2$CH$_2$OH | —SO$_2$CH$_3$ |
| —SO$_2$NH$_2$ | —SOCH$_2$CH$_2$OH |
| —NHCHO | —SO$_2$N(CH$_3$)$_2$ |
| —NHCO$_2$CH$_3$ | —NHCOCH$_3$ |
| —CN | —NHSO$_2$CH$_3$ |
| —C(O)CH$_3$ | —CHO |
| —CH=NOH | —COCH$_2$OH |
| —CH=NOCH$_2$CO$_2$Me | —CH=NOCH$_3$ |
| —SO$_2$CH$_2$CH$_2$OH | —CH=NOCMe$_2$CO$_2$Me |
| —CH=NOCMe$_2$CO$_2$ME | —CO$_2$CH$_2$CH$_2$OH |
| —C(O)NH$_2$ | —C(O)NHCH$_3$ |
| —C(O)N(CH$_3$)$_2$ | —C(O)NHCH$_2$CN |
| —C(O)NHCH$_2$CONH$_2$ | —C(O)NHCH$_2$CO$_2$Me |
| —C(O)NHOH | —C(O)NHCH$_3$ |
| -tetrzolyl | —CO$_2$Me |
| —SCF$_3$ | —PO$_3$HMe |
| —C(O)NHSO$_2$Ph | —C(O)NHSO$_2$NH$_2$ |
| —SO$_3$Me | —SO$_2$NHCN |
| —SO$_2$NHCOHN$_2$ | —CH=CHCN |
| —CH=CHC(O)NH$_2$ | —CH=CHCO$_2$Me |
| —C≡C—C(O)NH$_2$ | —C≡C—CN |
| —CH$_2$OH | —CH$_2$N$_3$ |
| —CH$_2$CO$_2$Me and | —CH$_2$I. |

6. The compound of claim 1, wherein Z represents —CH=CH—, —C(O)—, —O— or —S(O)$_x$ with x equal to 0, 1 or 2, and the group —(CH$_2$)$_m$—X—(CH$_2$)$_n$— represents: —CH$_2$—O—; —CH$_2$CH$_2$—; —CH$_2$NH—; —CH$_2$SO$_2$—; —CH$_2$C(O)—; —CH$_2$OC(O)— or —CH$_2$NHC(O)—.

7. The compound of claim 2, wherein one R$^a$ group is present and is selected from the group consisting of:

H; —CF$_3$; —Br; —I; —Cl; —F; —OC$_{1-4}$alkyl substituted with 1-3 R$^q$ groups, which are independently selected from —OH, —OCH$_3$, —CN, —F, —CF$_3$, and —COOM$^a$, where M$^a$ is H, alkali metal or methyl; and —OH.

8. The compound according to claim 4, wherein Y is Na$^+$ or K$^+$.

9. The compound in accordance with claim 1 wherein Y represents a pharmaceutically acceptable ester forming group.

10. The compound in accordance with claim 9 wherein the pharmaceutically acceptable ester forming group is a biolabile ester forming group.

11. A pharmaceutical composition comprising a compound in accordance with claim 1 in combination with a pharmaceutically acceptable carrier.

12. The pharmaceutical composition in accordance with claim 11 in the form of a tablet, capsule, solution or suspension.

13. A pharmaceutical composition comprising a compound in accordance with claim 1, and a DHP inhibitor in combination with a pharmaceutically acceptable carrier.

14. The pharmaceutical composition according to claim 13 wherein the DHP inhibitor is 7-(L-2-amino-2-carboxyethylthio)-2-(2, 2-dimethylcyclopropanecarboxamide)-2-heptenoic acid.

15. A method of treating a bacterial infection in a mammal in need of such treatment comprising administering to said mammal a compound in accordance with claim 1 in an amount effective to treat said bacterial infection.

16. A method of treating a bacterial infection in a mammalian subject in need of such treatment, comprising administering to such subject an antibacterially effective amount of a compound of claim 1 and an inhibitorily effective amount of a DHP inhibitor.

17. The method according to claim 16, wherein the DHP inhibitor is 7-(L-2-amino-2-carboxyethyl-thio)-2-(2, 2-dimethylcyclopropanecarboxamide)-2-heptenoic acid.

* * * * *

UNITED STATES PATENT AND TRADEMARK OFFICE
CERTIFICATE OF CORRECTION

PATENT NO. : 5,372,993

DATED : December 13, 1994

INVENTOR(S) : Frank DiNinno

It is certified that error appears in the above-indentified patent and that said Letters Patent is hereby corrected as shown below:

In claim 1, column 54, at line 8, after "C(O)-,", delete [ $-S(O)_xNR13$ ] and replace with -- $-S(O)_xNR^f-$ --.

In claim 1, column 54, at line 21, after "-F," delete [or] and insert -- and --.

Signed and Sealed this

Twenty-fifth Day of July, 1995

Attest:

BRUCE LEHMAN

*Attesting Officer*     *Commissioner of Patents and Trademarks*